US011160688B2

(12) United States Patent
Cho et al.

(10) Patent No.: US 11,160,688 B2
(45) Date of Patent: Nov. 2, 2021

(54) VISUAL AID DISPLAY DEVICE AND METHOD OF OPERATING THE SAME

(71) Applicant: SAMSUNG ELECTRONICS CO., LTD., Suwon-si (KR)

(72) Inventors: Jung-hoon Cho, Seoul (KR); Yong-nam Kim, Yongin-si (KR); Seung-chan Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 56 days.

(21) Appl. No.: 15/705,439

(22) Filed: Sep. 15, 2017

(65) Prior Publication Data

US 2018/0125716 A1    May 10, 2018

Related U.S. Application Data

(60) Provisional application No. 62/420,026, filed on Nov. 10, 2016.

(30) Foreign Application Priority Data

Feb. 24, 2017    (KR) .......................... 10-2017-0025055

(51) Int. Cl.
*A61F 9/08*    (2006.01)
*G02B 27/01*    (2006.01)
(Continued)

(52) U.S. Cl.
CPC .............. *A61F 9/08* (2013.01); *G02B 27/017* (2013.01); *G02B 27/0172* (2013.01);
(Continued)

(58) Field of Classification Search
CPC .............. G02B 27/017; G02B 27/0172; G02B 2027/014; G02B 2027/0138; A61F 9/08; A61B 3/02; G06T 19/006; G06T 5/001; G06T 11/00; G06T 11/60; G06K 9/36; G06K 9/605; G06K 2009/366;
(Continued)

(56) References Cited

U.S. PATENT DOCUMENTS 5,067,019 A * 11/1991 Juday .................... G06T 3/0018
                                                                348/580
6,160,576 A * 12/2000 Higuchi .................. G06T 5/001
                                                                348/62
(Continued)

FOREIGN PATENT DOCUMENTS

CA    2820241 A1 * 12/2013    ............. H04N 7/185
JP    5188507 B2    4/2013
(Continued)

*Primary Examiner* — William C Vaughn, Jr.
*Assistant Examiner* — Naod W Belai
(74) *Attorney, Agent, or Firm* — Sughrue Mion, PLLC

(57) ABSTRACT

A display device and an operating method thereof are provided. The display device may include: a display; a camera; a memory configured to store one or more instructions; and a processor configured to execute the instructions to obtain an image captured by the camera, transform the image based on visual condition information of a user, the visual condition information including information about a type of visual impairment of the user, and display the transformed image on the display.

20 Claims, 28 Drawing Sheets

(51) Int. Cl.
  *G06T 19/00* (2011.01)
  *G06K 9/36* (2006.01)
  *G09B 21/00* (2006.01)
  *G06F 3/048* (2013.01)
  *H04N 13/344* (2018.01)
  *G06F 3/01* (2006.01)
  *G06T 11/00* (2006.01)
  *G06K 9/60* (2006.01)
  *G06T 5/00* (2006.01)
  *G06T 11/60* (2006.01)

(52) U.S. Cl.
  CPC .............. *G06F 3/011* (2013.01); *G06F 3/048* (2013.01); *G06K 9/36* (2013.01); *G06K 9/605* (2013.01); *G06T 5/001* (2013.01); *G06T 11/00* (2013.01); *G06T 11/60* (2013.01); *G06T 19/006* (2013.01); *G09B 21/008* (2013.01); *H04N 13/344* (2018.05); *G02B 2027/0138* (2013.01); *G06K 2009/366* (2013.01)

(58) Field of Classification Search
  CPC .... G09B 21/008; H04N 13/344; G06F 3/048; G06F 3/011
  See application file for complete search history.

(56) References Cited

U.S. PATENT DOCUMENTS

| | | | | |
|---|---|---|---|---|
| 6,301,050 | B1* | 10/2001 | DeLeon | G02B 23/12 345/8 |
| 6,309,117 | B1* | 10/2001 | Bunce | A61B 3/032 351/237 |
| 6,591,008 | B1* | 7/2003 | Surve | G06T 5/001 348/62 |
| 6,611,618 | B1* | 8/2003 | Peli | G06T 5/10 345/632 |
| 6,766,495 | B1* | 7/2004 | Bates | G06F 17/212 715/201 |
| 6,912,301 | B1* | 6/2005 | Lin | G06T 7/0012 382/128 |
| 6,931,151 | B2* | 8/2005 | Weast | G06T 11/001 345/589 |
| 7,027,101 | B1* | 4/2006 | Sloo | H04N 5/44504 348/564 |
| 7,272,785 | B2* | 9/2007 | Fukuda | G06T 11/60 715/234 |
| 8,130,262 | B2* | 3/2012 | Behm | G09B 21/008 348/62 |
| 8,135,227 | B2* | 3/2012 | Lewis | G02B 27/017 382/254 |
| 8,438,470 | B2* | 5/2013 | Asakawa | G06F 40/14 715/234 |
| 8,494,298 | B2 | 7/2013 | Lewis et al. | |
| 8,712,193 | B2* | 4/2014 | Boncyk | A63F 13/65 382/103 |
| 8,908,987 | B1* | 12/2014 | Krishnaswamy | G06T 5/00 382/260 |
| 9,032,020 | B2* | 5/2015 | Gregg | H04N 21/222 709/203 |
| 9,233,026 | B2 | 1/2016 | Ziemeck et al. | |
| 9,501,830 | B2* | 11/2016 | Teomim | G06T 5/002 |
| 9,516,283 | B2* | 12/2016 | Hilkes | G02B 27/017 |
| 9,952,434 | B2* | 4/2018 | Jiao | G02B 27/0081 |
| 9,955,862 | B2* | 5/2018 | Freeman | G06F 19/00 |
| 10,872,472 | B2* | 12/2020 | Watola | G06F 3/011 |
| 2003/0197693 | A1* | 10/2003 | Karstens | A61B 3/063 345/204 |
| 2004/0136570 | A1* | 7/2004 | Ullman | G06T 5/004 382/114 |
| 2004/0227911 | A1* | 11/2004 | Salvatori | H04N 9/3182 353/122 |
| 2005/0168569 | A1* | 8/2005 | Igarashi | A61F 9/08 348/62 |
| 2005/0281470 | A1* | 12/2005 | Adams | H04N 21/25875 382/232 |
| 2006/0015342 | A1* | 1/2006 | Kurzweil | G09B 21/006 704/260 |
| 2006/0098089 | A1* | 5/2006 | Sofer | G09B 21/006 348/62 |
| 2007/0257934 | A1* | 11/2007 | Doermann | G06K 9/36 345/606 |
| 2007/0286596 | A1* | 12/2007 | Lonn | H04N 1/00387 396/429 |
| 2008/0247620 | A1* | 10/2008 | Lewis | G06T 19/006 382/128 |
| 2009/0067715 | A1* | 3/2009 | Spruck | G06T 7/12 382/172 |
| 2009/0089322 | A1* | 4/2009 | Naaman | G06F 16/48 |
| 2009/0096808 | A1* | 4/2009 | Winn | G06T 11/60 345/594 |
| 2009/0113477 | A1* | 4/2009 | Yang | H04N 21/485 725/40 |
| 2009/0123036 | A1* | 5/2009 | Huang | A61B 3/1225 382/117 |
| 2010/0177179 | A1* | 7/2010 | Behm | G06F 1/163 348/62 |
| 2010/0235768 | A1* | 9/2010 | Agevik | H04M 1/72544 715/763 |
| 2011/0043644 | A1* | 2/2011 | Munger | H04N 5/23296 348/207.1 |
| 2011/0134318 | A1* | 6/2011 | Chang | H04N 7/18 348/448 |
| 2011/0216179 | A1* | 9/2011 | Dialameh | A61F 9/08 348/62 |
| 2012/0147163 | A1* | 6/2012 | Kaminsky | G09G 5/028 348/62 |
| 2012/0242801 | A1* | 9/2012 | Barnes | A61N 1/36046 348/46 |
| 2012/0262477 | A1* | 10/2012 | Buchheit | G09G 5/00 345/619 |
| 2012/0268608 | A1* | 10/2012 | Watanabe | H04N 5/232 348/169 |
| 2013/0035742 | A1* | 2/2013 | Talbot | G06K 9/00228 607/54 |
| 2013/0120390 | A1* | 5/2013 | Marchand | G06T 5/003 345/428 |
| 2013/0208234 | A1* | 8/2013 | Lewis | G06F 3/011 351/158 |
| 2013/0215147 | A1* | 8/2013 | Hilkes | G02B 27/017 345/633 |
| 2013/0250078 | A1* | 9/2013 | Levy | A61F 9/08 348/62 |
| 2013/0286045 | A1* | 10/2013 | Kweon | G06T 19/006 345/633 |
| 2013/0289668 | A1* | 10/2013 | Nirenberg | A61N 5/0622 607/88 |
| 2014/0085446 | A1* | 3/2014 | Hicks | G09B 21/008 348/62 |
| 2014/0210970 | A1* | 7/2014 | Dalal | A61F 9/08 348/62 |
| 2014/0253701 | A1* | 9/2014 | Wexler | H04M 1/72403 348/62 |
| 2014/0267643 | A1* | 9/2014 | Wexler | G06F 3/16 348/62 |
| 2014/0282285 | A1* | 9/2014 | Sadhvani | G06F 3/04847 715/865 |
| 2014/0341442 | A1* | 11/2014 | Lewis | G06K 9/00248 382/118 |
| 2015/0081699 | A1* | 3/2015 | Leppanen | G06F 16/44 707/736 |
| 2015/0161474 | A1* | 6/2015 | Jaber | G06K 9/52 382/203 |
| 2015/0192776 | A1* | 7/2015 | Lee | A61B 3/066 345/690 |
| 2015/0235427 | A1* | 8/2015 | Nobori | G06T 19/006 345/629 |
| 2015/0238362 | A1* | 8/2015 | Chayet | G02B 26/101 348/63 |

(56) References Cited

U.S. PATENT DOCUMENTS

| | | | | |
|---|---|---|---|---|
| 2015/0355481 | A1* | 12/2015 | Hilkes | G02B 27/017 351/204 |
| 2016/0055657 | A1* | 2/2016 | Beyrak | G06F 3/04897 345/594 |
| 2016/0062454 | A1 | 3/2016 | Wang et al. | |
| 2016/0104453 | A1* | 4/2016 | Borenstein | H04N 13/257 348/62 |
| 2016/0119554 | A1* | 4/2016 | Matsuhashi | H04L 67/02 348/231.3 |
| 2016/0156850 | A1* | 6/2016 | Werblin | G02B 27/017 348/63 |
| 2016/0310325 | A1* | 10/2016 | Jiao | G02B 27/0081 |
| 2016/0314564 | A1* | 10/2016 | Jones | G02B 13/007 |
| 2016/0335917 | A1* | 11/2016 | Lydecker | G06T 19/006 |
| 2017/0017831 | A1* | 1/2017 | Rollend | G06K 9/00228 |
| 2017/0200296 | A1* | 7/2017 | Jones | G06F 40/58 |
| 2017/0232334 | A1* | 8/2017 | Tokunaga | A63F 13/655 463/31 |
| 2017/0235161 | A1* | 8/2017 | Hilkes | G02C 13/005 351/204 |
| 2017/0248788 | A1* | 8/2017 | Osterhout | H04N 7/183 |
| 2018/0036175 | A1* | 2/2018 | Rollend | B23K 9/167 |
| 2018/0104106 | A1* | 4/2018 | Lee | G06T 1/0007 |
| 2018/0125716 | A1* | 5/2018 | Cho | G02B 27/017 |
| 2018/0137358 | A1* | 5/2018 | Rousseau | G06K 9/00664 |
| 2018/0181832 | A1* | 6/2018 | Wu | G06Q 30/00 |
| 2018/0225361 | A1* | 8/2018 | Skarin | G06Q 10/10 |
| 2018/0249151 | A1* | 8/2018 | Freeman | G06F 1/163 |
| 2018/0365877 | A1* | 12/2018 | Watola | G06T 11/60 |
| 2019/0014380 | A1* | 1/2019 | Candelore | H04N 21/6587 |
| 2019/0079291 | A1* | 3/2019 | Joos | G09B 21/008 |
| 2019/0286227 | A1* | 9/2019 | Samadani | G06T 3/40 |
| 2019/0294909 | A1* | 9/2019 | Wexler | G06K 9/3275 |

FOREIGN PATENT DOCUMENTS

| | | |
|---|---|---|
| JP | 2015-57659 A | 3/2015 |
| KR | 10-2009-0105531 A | 10/2009 |
| KR | 10-1655792 B1 | 9/2016 |

* cited by examiner

VISUAL AID DISPLAY DEVICE AND METHOD OF OPERATING THE SAME

CROSS-REFERENCE TO RELATED APPLICATIONS

This application claims the benefit of U.S. Provisional Patent Application No. 62/420,026, filed on Nov. 10, 2016 in the U.S. Patent and Trademark Office, and priority from Korean Patent Application No. 10-2017-0025055, filed on Feb. 24, 2017 in the Korean Intellectual Property Office, the disclosures of which are incorporated herein in their entireties by reference.

BACKGROUND

1. Field

Apparatuses and methods consistent with example embodiments relate to visual aid display devices and methods of operating the same, and more particularly, to visual aid display devices that provide transformed images for users with low vision and methods of operating the visual aid display devices.

2. Description of the Related Art

As various devices including mobile phones provide an increasing variety of complex functions, applications for these technologies have also diversified. As wearable devices that may be worn on a user's body are developed, these devices have also been customized for each user's individual needs.

Recently, as multimedia technology, network technology, and image processing technology have advanced, it has become possible to provide environments and user interfaces that are better suited for users with special visual conditions.

The recent developments in virtual reality (VR) technology has also enabled further customization using VR devices.

SUMMARY

Example embodiments provide visual aid display devices that provide transformed images for users with low vision and methods of operating the visual aid display devices.

According to an aspect of an example embodiment, there is provided a display device including: a display; a camera; a memory configured to store one or more instructions; and a processor configured to execute the instructions to: obtain an image captured by the camera, transform the image based on visual condition information of a user, the visual condition information including information about a type of visual impairment of the user, and display the transformed image on the display.

According to an aspect of another example embodiment, there is provided a method of operating a display device including: obtaining an image by capturing the image with a camera included in the display device; transforming the image, based on visual condition information of a user, the visual condition information including information about a type of visual impairment of the user; and displaying the transformed image on a display of the display device.

According to an aspect of another example embodiment, there is provided a non-transitory computer-readable recording medium having recorded thereon instructions which, when executed by a processor, cause the processor to perform the above method.

BRIEF DESCRIPTION OF THE DRAWINGS

The above and/or other aspects will become apparent and more readily appreciated from the following description of example embodiments, taken in conjunction with the accompanying drawings in which.

DETAILED DESCRIPTION

Figure 1:
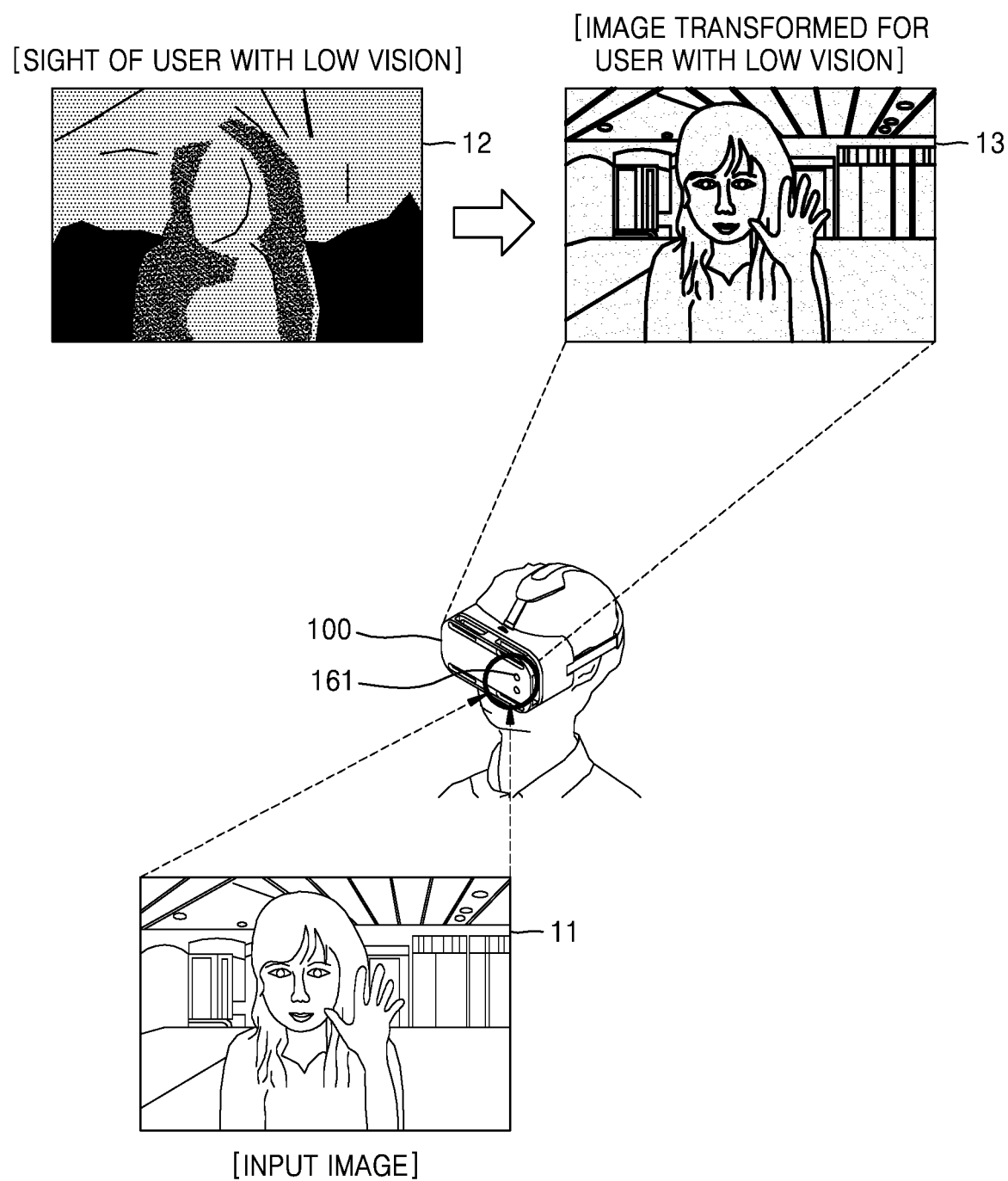
FIG. 1 is a diagram of a method of operating a display device, according to an example embodiment.

Reference will now be made in detail to example embodiments, which are illustrated in the accompanying drawings, wherein like reference numerals refer to like elements throughout. In this regard, the present embodiments may have different forms and should not be construed as being limited to the descriptions set forth herein. Accordingly, the example embodiments are merely described below, by referring to the figures, to explain aspects. Also, parts in the drawings unrelated to the detailed description are omitted to ensure clarity of the present disclosure. As used herein, the term "and/or" includes any and all combinations of one or more of the associated listed items. Expressions such as "at least one of," when preceding a list of elements, modify the entire list of elements and do not modify the individual elements of the list.

The terms used in the present disclosure are selected from among common terms that are currently widely used in consideration of their function in the present disclosure. However, the terms may be different according to an intention of one of ordinary skill in the art, a precedent, or the advent of new technology. Therefore, the terms used in the present disclosure are not merely designations of the terms, but the terms are defined based on the meaning of the terms and contents throughout the present disclosure.

It will be understood that, although the terms "first," "second," etc. may be used herein to describe various elements, these elements should not be limited by these terms. These terms are only used to distinguish one element from another.

The terminology used herein is for the purpose of describing particular embodiments only and is not intended to be limiting of the present disclosure. As used herein, the singular forms "a," "an," and "the" are intended to include the plural forms as well, unless the context clearly indicates otherwise, and vice versa. Throughout the specification, it will be understood that when a portion is referred to as being "connected" to another portion, it may be "directly connected" to the other portion or may be "electrically connected" to the other portion with another device therebetween. It will be further understood that when a portion "includes" or "comprises" an element, unless otherwise defined, the portion may further include another element, not excluding the other element.

The term "the" and similar referents used herein, especially, in the appended claims, may cover both the singular and the plural. The steps of methods according to the present disclosure can be performed in any suitable order unless clearly specified herein. The present disclosure is not limited by the description order of stated steps.

In the present specification, the description "A may include one of a1, a2, and a3" has a broad meaning that an example element that may be included in element A is a1, a2, or a3.

An element that may constitute the element A is not necessarily limited to a1, a2, or a3 by the above description. Accordingly, it should be noted that the element that may constitute the element A is not exclusively construed as excluding other elements that are not given as examples in addition to a1, a2, and a3.

Also, the above description means that A may include a1, may include a2, or may include a3. The above description does not mean that elements constituting A are selectively determined essentially within a predetermined set. For example, it should be noted that the description is not construed in a narrow sense as meaning that a1, a2, or a3 selected from a set essentially including a1, a2, and a3 constitutes component A.

Phrases such as "in some example embodiments" or "in an example embodiment" appearing in various places herein do not all necessarily refer to the same embodiment. In other words, one or more features that are described in terms of one example embodiment may be combined with one or more other features that are described in terms of another example embodiment.

Some example embodiments of the present disclosure may be described in terms of functional block components and various processing steps. Some or all of the functional blocks may be realized by any number of hardware and/or software components configured to perform specific functions. For example, functional blocks of the present disclosure may be implemented by one or more microprocessors or may be implemented by circuit components for predetermined function. In addition, for example, functional blocks of the present disclosure may be implemented with any programming or scripting language. Functional blocks may be implemented in algorithms that execute on one or more processors. Furthermore, the present disclosure may employ any number of conventional techniques for electronics configuration, signal processing and/or data processing and the like. The words "mechanism," "element," "means," and "component" may be used broadly and are not limited to mechanical and physical components.

The term "unit" or "module" used herein refers to an unit for processing at least one function or operation, and the unit may be implemented as hardware, as software, or as a combination of hardware and software. The "unit" or "module" may be stored in an addressable storage medium or may be implemented by a program that may be executed by a processor. For example, the "unit" or "module" may be implemented by elements such as software elements, object-oriented software elements, class elements, and task elements, processes, functions, attributes, procedures, subroutines, segments of program code, drivers, firmware, micro codes, circuits, data, a database, data structures, tables, arrays, and variables.

Furthermore, the connecting lines or connectors shown in the various figures presented are intended to represent exemplary functional relationships and/or physical or logical couplings between the various elements. It should be noted that many alternative or additional functional relationships, physical connections or logical connections may be present in a practical device.

Hereinafter, the present disclosure will be described in detail with reference to the accompanying drawings.

FIG. 1 is a diagram of a method of operating a display device, according to an example embodiment.

Figure 26:
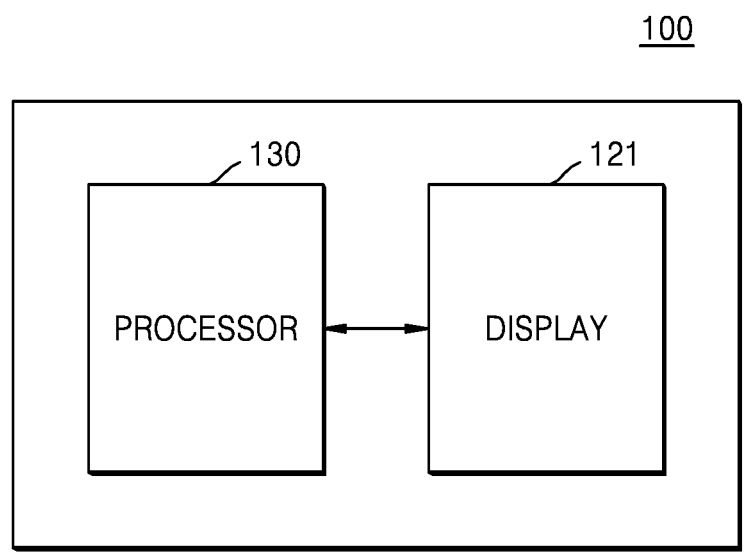
FIGS. 26 and 27 are block diagrams of a display device according to an example embodiment.

According to an aspect of an example embodiment, a display device 100 may transform an image 11 captured by a camera 161 based on visual condition information of a user and then may display a transformed image 13 on a display (e.g., a display 121 of FIG. 26).

For example, for a person with an visual condition, of which vision correction is difficult to achieve with conventional eyeglasses, it may be difficult for the user to recognize objects via an image 12 that is visually perceived by the user. According to an aspect of an example embodiment, the display device 100 may display, on the display 121, the transformed image 13 based on visual condition information of the user, and thus, the user wearing the display device 100 may recognize objects more clearly. For example, the user may place the display device 100 over his or her head and may see, via the display 121, a transformed image according to the visual condition of the user.

A processor (e.g., a processor 130 of FIG. 26) of the display device 100 may extract outlines of an object included in an image and may provide an image transformed via contrast adjustment between the outlines and the other regions, and thus, the user with low vision may recognize the object included in the image more clearly. In addition, for example, the processor 130 of the display device 100 may transform an input image into a binary image (e.g., a black-and-white image, a high-contrast image, etc.) and may provide the binary image, thereby assisting the user's object recognition.

Visual condition information may include information regarding a type of visual impairment or eye disorder of the user and a degree of visual impairment according to the type of visual impairment.

For example, the type of visual impairment may include low or blurry vision, myopia, hyperopia, color blindness/weakness, metamorphopsia, central scotoma, and tunnel vision.

For example, in the case of low vision, the degree of visual impairment according to the type of visual impairment may refer to a visual acuity. As another example, in the case of color blindness, the degree of visual impairment according to the type of visual impairment may be one of red-green color blindness, blue-yellow color blindness, and total color blindness. In the case of central scotoma, the degree of visual impairment according to the type of visual impairment may refer to a location, a shape, and a size of scotoma. However, the degree of visual impairment according to the type of visual impairment is not limited thereto.

In addition, the display device 100 may transform not only an image captured by the camera 161 but also an image stored in a memory (e.g., a memory 170 of FIG. 27) of the display device 100 and an image received from an external device according to the visual condition of the user and may provide the images.

The display device 100 may be a head-mounted display (HMD), such as a virtual reality (VR) headset, or an eyeglass-type device, such as smart glasses, but is not limited thereto. For example, the HMD may have a built-in display 121 or may be equipped with a smartphone so that a display of the smartphone may be used as the display 121. The viewing surface of the display 121 may be placed at a short distance away (e.g., within 10 centimeters) from the user's eyes such that the images displayed on the display 121 may cover all or substantially all of the user's field of vision. Optical lenses and/or eyepieces may be disposed between the display 121 and the user's eyes to help the user focus on the displayed images.

The display device 100 may provide a VR image to the user, but a type of an image which is provided by the display device 100 is not limited thereto.

The VR image may be an image that gives the user an illusion of seeing an actual surrounding environment via a sense of sight, a sense of hearing, or the like of the user by using captured or computer-generated imagery.

An image provided by the display device 100 may be a stereoscopic three-dimensional (3D) image. Stereoscopic 3D allows a viewer to experience a sense of depth by respectively presenting a pair of 2D images having binocular disparity to both eyes of the viewer.

The display 121 may be divided into two screens (or two portions of a single screen) to display a left-eye image and a right-eye image. For example, the display 121 may implement a stereoscopic image effect according to a field sequential stereoscopic method that creates a stereoscopic image effect by alternately displaying a left-eye image and a right-eye image, but is not limited thereto.

In addition, an image provided by the display device 100 may be an augmented reality image. The augmented reality image may be an image displayed by overlaying a 3D virtual image on a real-life image captured by the camera 161.

FIG. 1 illustrates an example embodiment but is not limited thereto.

Figure 2:
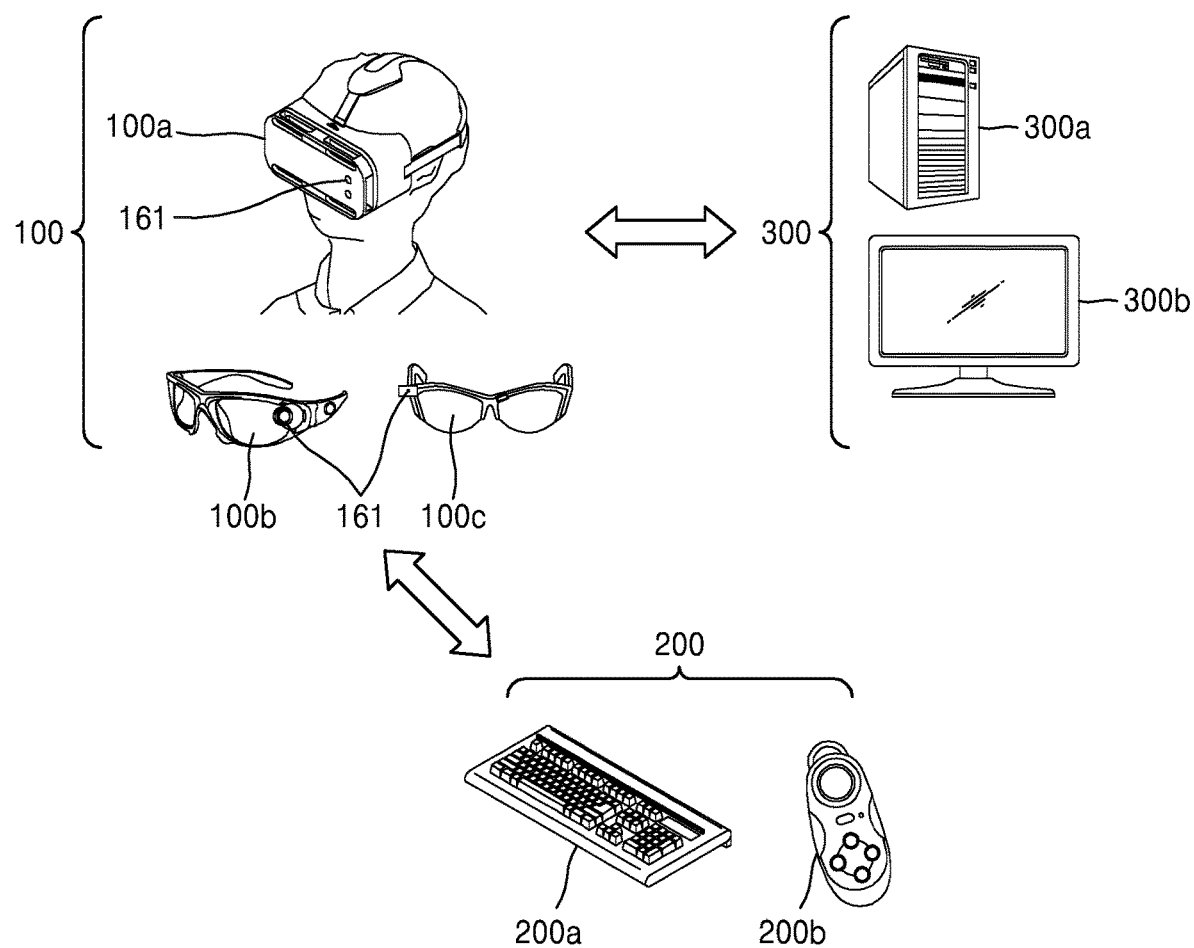
FIG. 2 is a diagram of a method of operating a display device, a control device, and an external device, according to an example embodiment.

FIG. 2 is a diagram of a method of operating a display device, a control device, and an external device related to an example embodiment.

According to an aspect of an example embodiment, the display device 100 may be a VR headset 100a, an eyeglass-type wearable device 100b, an eyeglass-type device 100c equipped with a transparent display, or a head-mounted display but is not limited thereto.

In addition, the display device 100 may be implemented as various electronic devices such as a cellular phone, a tablet personal computer (PC), a digital camera, a camcorder, a laptop computer, a desktop computer, an e-book terminal, a digital broadcast terminal, a personal digital assistant (PDA), a portable multimedia player (PMP), a navigation system, a digital music player, or a wearable device.

An external device 300 may be a server 300a or another display device 300b (e.g., a television), capable of providing image content to the display device 100, but is not limited thereto.

In addition, the external device 300 may be a digital broadcast receiver capable of receiving digital broadcasting. In addition, the external device 300 may be a reproducing device that reproduces (e.g., plays) multimedia content. For example, the external device 300 may be a Blu-ray Disc player, a set-top box, a digital versatile disc (DVD) player, a streaming device, a digital media player, or a home theater. Alternatively, the external device 300 may be implemented as various electronic devices such as a smartphone, a tablet PC, a mobile phone, a video phone, an e-book reader, a desktop PC, a laptop PC, a netbook computer, a PDA, a PMP, a digital music player, or a wearable device.

The display device 100 and the external device 300 may transmit and receive data, signals, etc. by using wired and/or wireless communication. For example, the server 300a may transmit image content to the display device 100.

In response to a request signal of the display device 100, the server 300a may transform an image based on image transformation information and may provide a transformed image to the display device 100.

In addition, for example, the server 300a may receive visual condition information of a user from the display device 100 and may transmit image transformation information based on the visual condition information to the display device 100.

A control device 200 may be implemented as various forms of devices for controlling the display device 100, such as a remote control 200b, a keyboard 200a, or a cellular phone.

The control device 200 may control the display device 100 by using short-range communication including infrared (IR), Wi-Fi, or Bluetooth. The control device 200 may control a function of the display device 100 by using at least one of a provided key (e.g., a button), a touchpad, a microphone capable of receiving the user's voice, and a sensor capable of recognizing motion of the control device 200.

The control device 200 may include a power on/off button for turning on or off the display device 100. Based on a user input, the control device 200 may also perform zoom-in/out of a display of the display device 100, contrast adjustment, color sharpness adjustment, chroma adjustment, color temperature adjustment, setting of visual condition information and image transformation information, or the like.

FIG. 2 illustrates an example embodiment but is not limited thereto.

Figure 3:
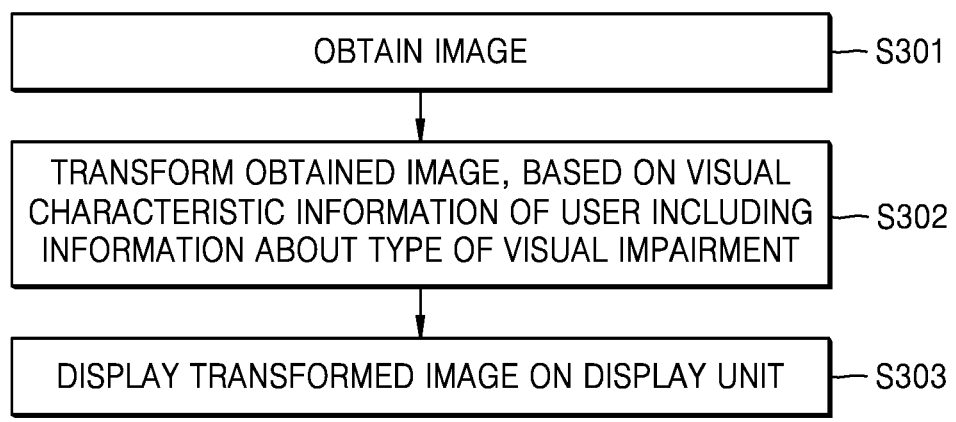
FIG. 3 is a flowchart of a method of operating a display device, according to an example embodiment.

FIG. 3 is a flowchart of a method of operating a display device according to an example embodiment.

In operation S301, the display device 100 may obtain an image to be displayed on the display 121.

The display device 100 may capture an image in real time via the camera 161. In addition or alternatively, the display device 100 may receive image content from the external device 300 via a communication interface (e.g., a communication interface 150 of FIG. 27). In addition, the display device 100 may determine an image stored in the memory 170 as an image to be displayed on the display 121.

In operation S302, the display device 100 may transform the obtained image, based on visual condition information of a user including a type of visual impairment.

For example, the visual condition information of the user may include low vision, color weakness/blindness, metamorphopsia, central scotoma, and/or tunnel vision.

The processor 130 of the display device 100 may determine image transformation information for transforming the obtained image, based on visual condition information.

The image transformation information may include an image transformation value for allowing the user to recognize an image more clearly based on visual condition information of the user. For example, the image transformation information may include a transformation value related to transformation into a binary image, enlargement or reduction of an object included in an image, display location change, contrast adjustment of an outline of an object, color sharpness adjustment, chroma adjustment, color temperature adjustment, etc.

The processor 130 of the display device 100 may transform the obtained image, based on the image transformation information.

For example, the display device 100 may transform the color of an image, based on the image transformation information including a color transformation value of the image. In addition, for example, the display device 100 may transform a display location of an image (or a portion of the image) to another region from among regions of the display 121 to avoid the region corresponding to central scotoma of the user, based on the image transformation information including a display location change value (e.g., coordinates) of the image.

In operation S303, the display device 100 may display a transformed image on the display 121.

For example, as the display device 100 transforms an image captured by the camera 161 in real time, based on the image transformation information, and provides a transformed image, the user with low vision, who is wearing the display device 100 (e.g., a VR headset) may recognize things more clearly.

In addition, for example, the display device 100 may transform image content received from the external device 300, based on visual condition of the user with low vision, and provide transformed image content, and thus, the user may watch image content which is recognized more clearly via the display device 100.

FIGS. 4 to 9 are diagrams of examples of providing an image transformed based on visual condition information of a user.

According to an aspect of an example embodiment, the visual condition information may include at least one of a type of visual impairment and a degree of visual impairment according to the type of visual impairment.

Figure 4:
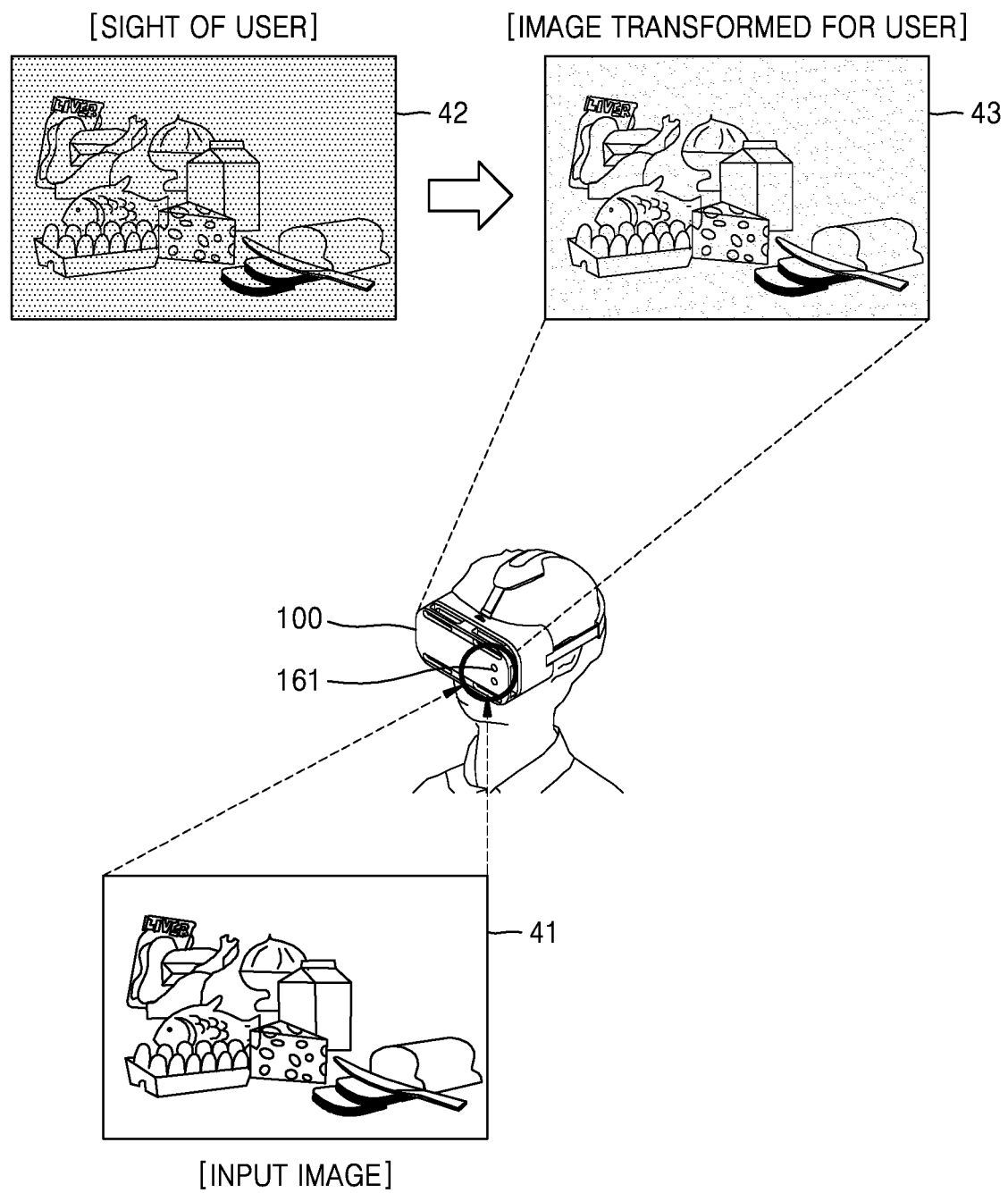
FIGS. 4 to 9 are diagrams of examples of providing an image transformed based on visual condition information of a user.

FIG. 4 illustrates an example of transforming and providing an image, based on visual condition information of a user having a color blindness symptom. As illustrated in FIG. 4, it may be difficult to distinguish the color of an object in an image 42 that is visually perceived by the user having a color blindness symptom.

The display device 100 may provide a transformed image 43 so that the user with a color blindness symptom may distinguish the color of an object in an input image 41 captured by the camera 161.

The processor 130 of the display device 100 may determine a transformation value for removing a certain color and highlighting another color as image transformation information, based on a degree of color blindness (e.g., red-green color blindness, blue-yellow color blindness, total color blindness). In addition, for example, the processor 130 of the display device 100 may determine a transformation value regarding a RGB color filter and a transformation value regarding adjustment of color temperature according to a surrounding light source as image transformation information. The processor 130 may display the image 43 transformed according to the determined image transformation information on the display 121.

Figure 5:
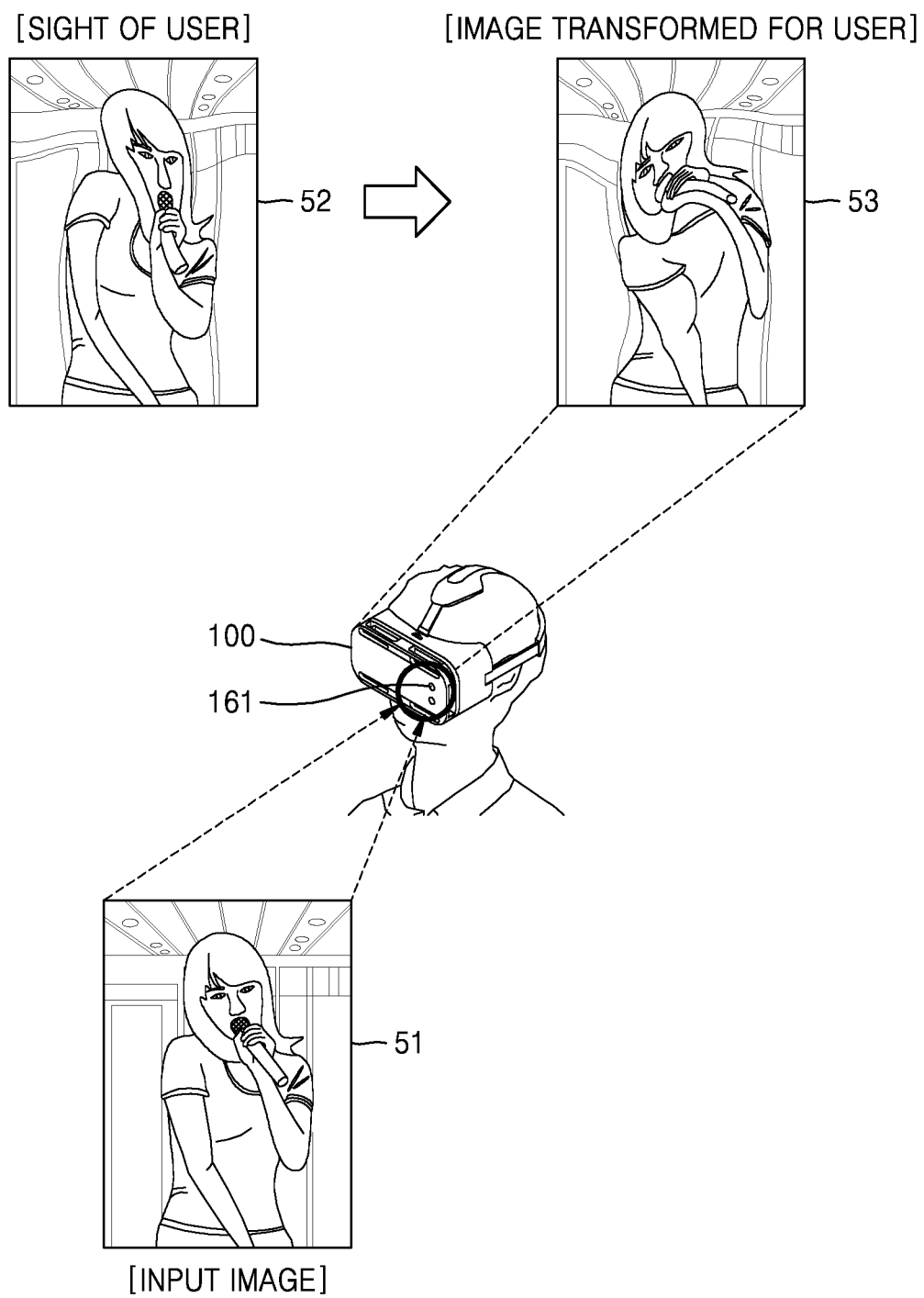

FIG. 5 illustrates an example of transforming and providing an image, based on visual condition information of a user with metamorphopsia. Metamorphopsia is a phenomenon in which objects within a field of vision look crooked or warped. As illustrated in FIG. 5, a portion of the field of vision may look contorted in an image 52 that is visually perceived by the user with metamorphopsia.

The display device 100 may provide a transformed image 53 so that an input image 51 captured by the camera 161 does not look distorted to the user with metamorphopsia.

The processor 130 of the display device 100 may determine a transformation value for correcting a region that looks contorted as image transformation information, based on a degree of metamorphopsia (e.g., a degree to which things look contorted, and a location, a size, a shape, etc. of a region in the field of vision looking contorted). The processor 130 may display the image 53 transformed according to the determined image transformation information on the display 121. For example, the transformed image 53 may be an image transformed by applying distortion in an inverse direction for the user with metamorphopsia.

Figure 6:
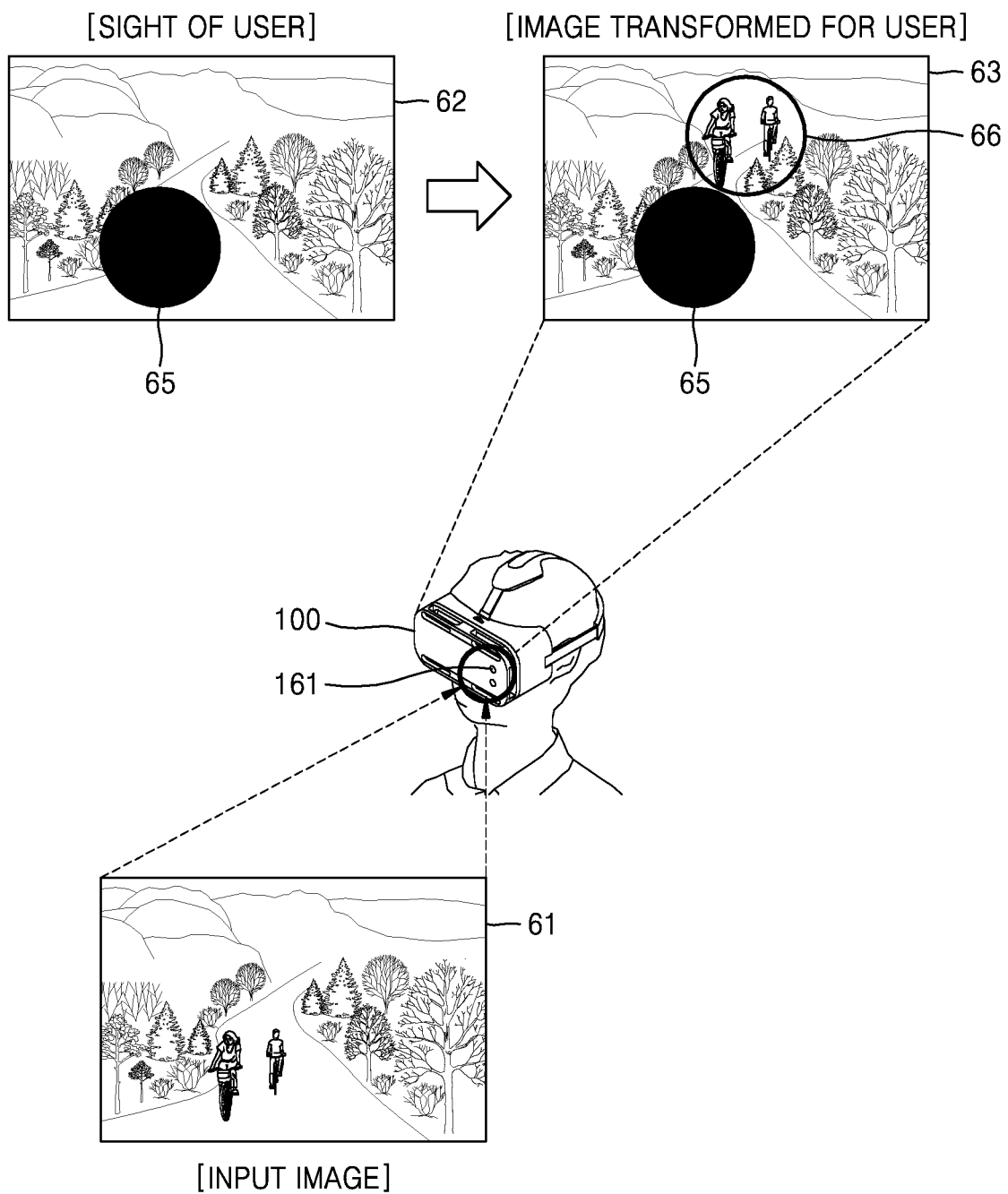

FIG. 6 illustrates an example of transforming and providing an image, based on visual condition information of a user having a central scotoma symptom. Central scotoma is a phenomenon in which a central region of the field of vision of the user is obscured due to macular degeneration, and a shape of a scotoma (e.g., an area of alteration in the field of vision) may have a circular shape, an oval shape, a racket shape, etc. As illustrated in FIG. 6, a portion of the central region of the field of vision may be obscured in an image 62 that is visually perceived by the user with macular degeneration.

The display device 100 may provide a transformed image 63 so that an image of the central region invisible to the user with a central scotoma symptom may be seen at a different location in an input image 61 captured by the camera 161. For example, a central scotoma region 65 that is invisible to the user may be displayed at a portion 66 of a region that is visible to the user.

The processor 130 of the display device 100 may determine a transformation value regarding a change of a display location of an image corresponding to a central scotoma region as image transformation information, based on a degree of central scotoma (e.g., a location, a size, a shape, etc. of central scotoma). For example, the image transformation information may include information regarding a location, a size, and a shape of a region to be displayed by changing a location of a portion the image corresponding to the central scotoma region.

The processor 130 may display the image 63 transformed according to the determined image transformation information on the display 121.

Figure 7:
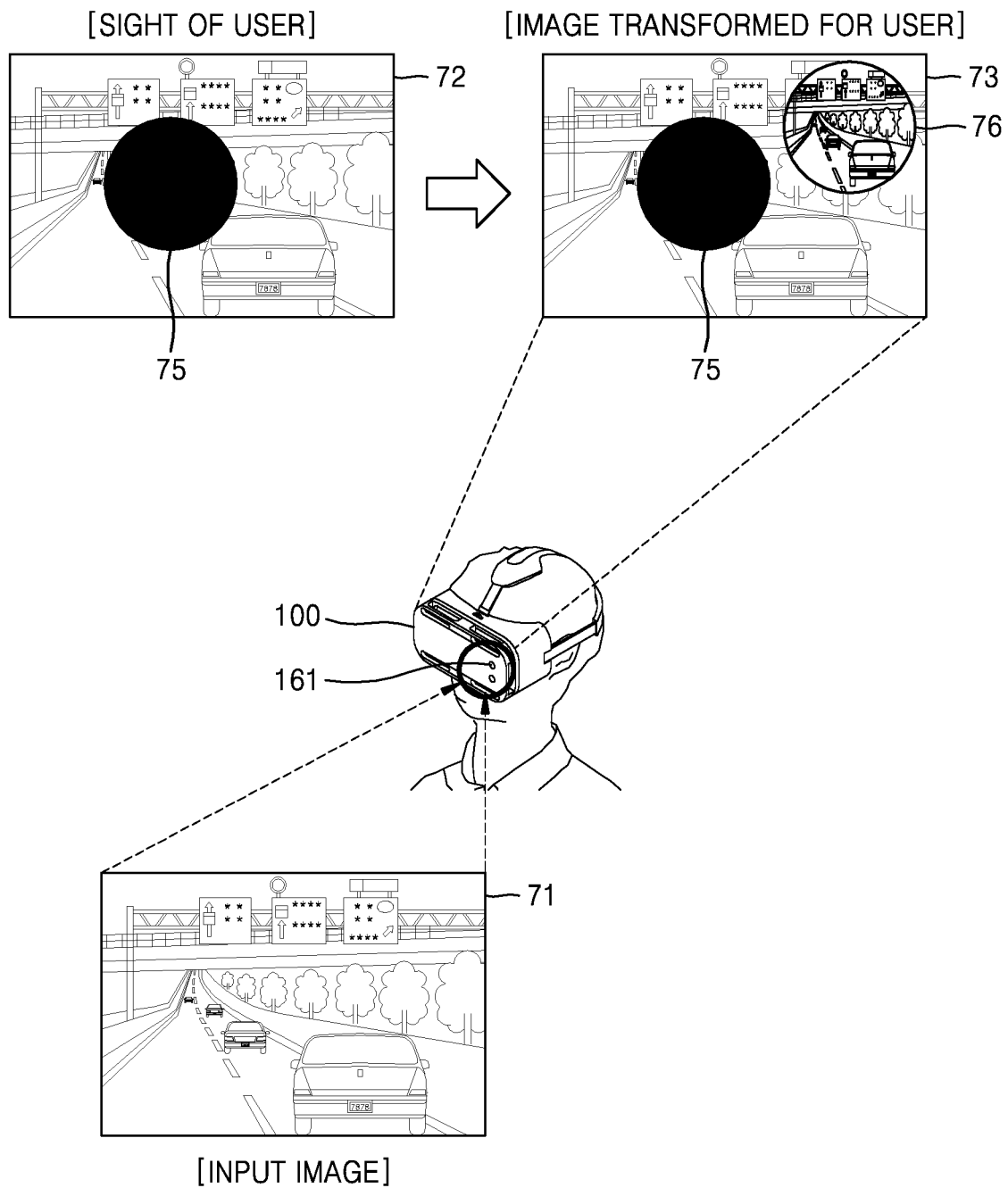

FIG. 7 illustrates another example of transforming and providing an image, based on visual condition information of a user having a central scotoma symptom.

As illustrated in FIG. 7, a portion of a central region of the field of vision may be obscured in an image 72 that is visually perceived by the user having a central scotoma symptom. The display device 100 may provide a transformed image 73 so that a portion of an image of the central region invisible to the user with a central scotoma symptom may be seen at a different location in an input image 71 captured by the camera 161. For example, a central scotoma region 75 that is invisible to the user may be displayed on a portion 76 of a region that is visible to the user.

The processor 130 of the display device 100 may determine a transformation value for displaying an entire image in the field of vision of the user, including a region corresponding to a central scotoma region, on some of the other regions except the central scotoma region as image transformation information, based on a degree of central scotoma (e.g., a location, a size, a shape, etc. of central scotoma). For example, the image transformation information may include information regarding a location, a size, and a shape for displaying the entire image of the field of vision of the user.

The processor 130 may display the image 73 transformed according to the determined image transformation information on the display 121.

Figure 8:
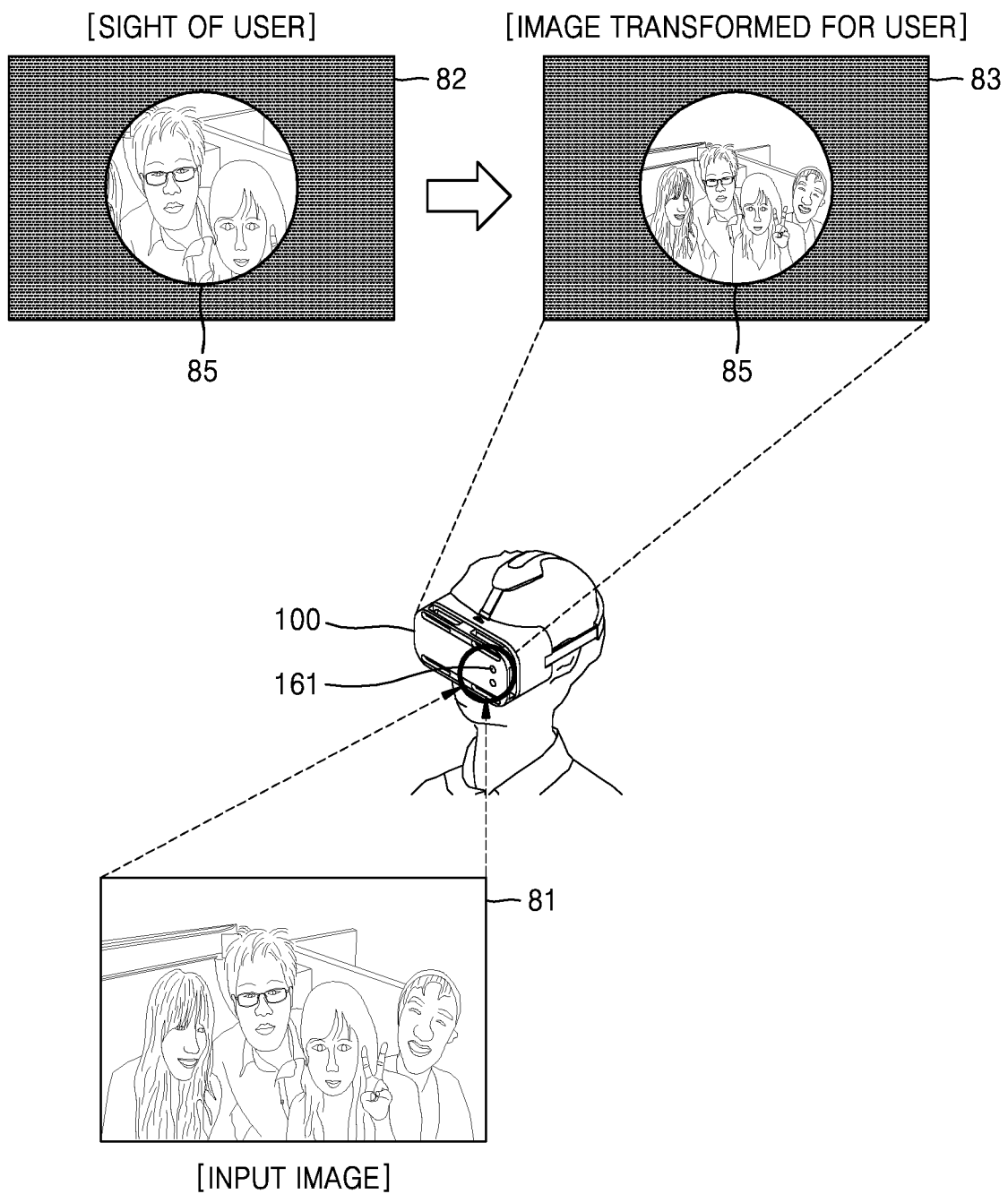

FIG. 8 illustrates an example of transforming and providing an image, based on visual condition information of a user having a tunnel vision symptom. Tunnel vision is a phenomenon in which vision is limited to the shape of a tunnel entrance as if the objects are observed through a tunnel. As illustrated in FIG. 8, a peripheral region except a central portion may be obscured in an image 82 that is visually perceived by the user having a tunnel vision symptom.

According to an aspect of an example embodiment, the display device 100 may provide a transformed image 83 so that an input image 81 captured by the camera 161 may be seen via a central region 85 that is visible to the user.

The processor 130 of the display device 100 may determine a transformation value for displaying an entire input image within a region visible to the user as image transformation information, based on the severity of a tunnel vision symptom (e.g., a location, a size, a shape, etc. of a tunnel vision region). For example, the image transformation information may include information regarding a location, a size, and a shape for displaying an entire image in the field of vision of the user.

The processor 130 may display the image 83 transformed according to the determined image transformation information on the display 121.

Figure 9:
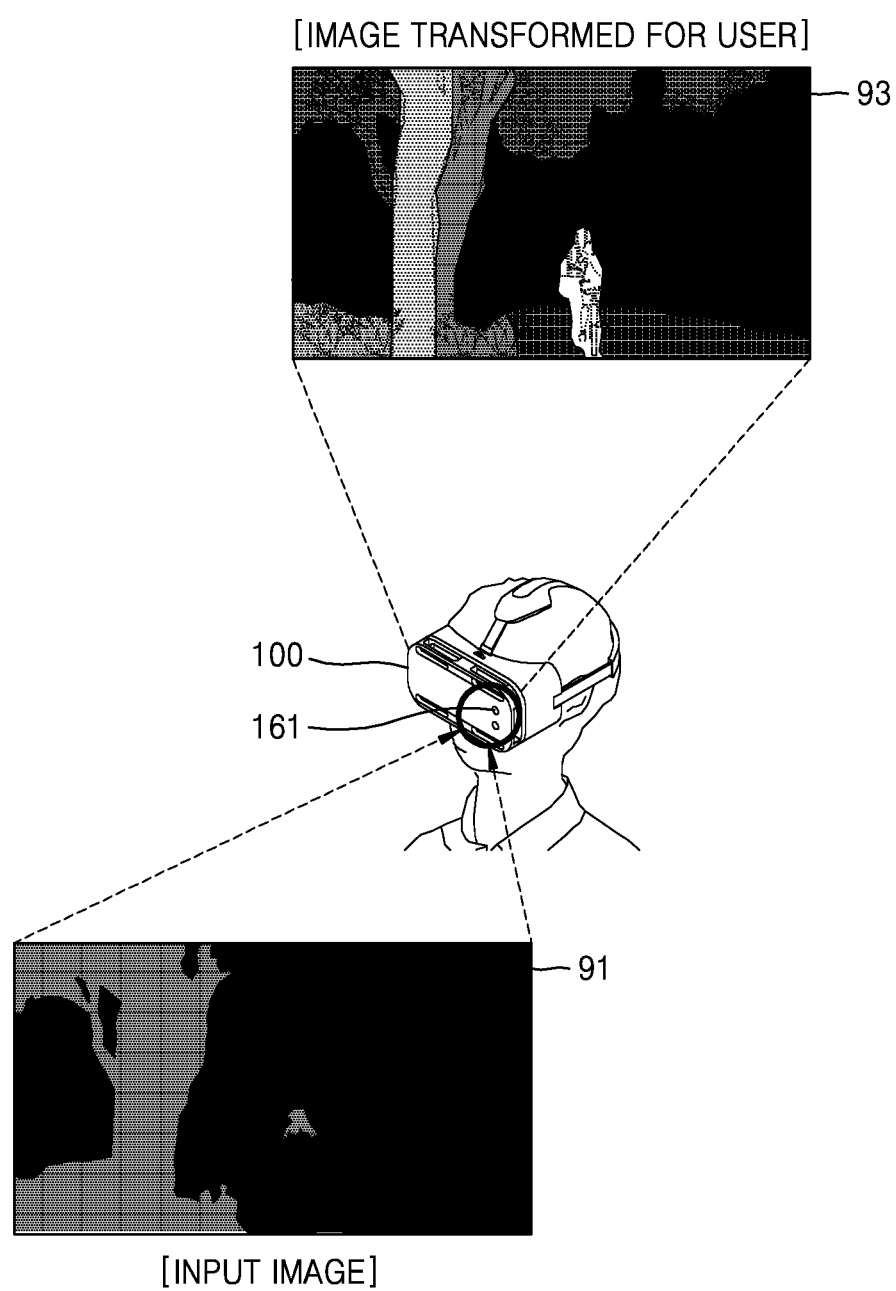

FIG. 9 shows an example of transforming and providing an image, based on visual condition information of a user, in an environment with low illumination intensity (e.g., low light condition). As illustrated in FIG. 9, it may be difficult for the user to recognize objects in an image 91 that is input in the environment with low illumination intensity.

According to an aspect of an example embodiment, the display device 100 may provide a transformed image 93 so that an object in the input image 91 captured by the camera 161 may be recognized.

The processor 130 of the display device 100 may change and determine, in the environment with low illumination intensity, image transformation information determined based on visual condition information of the user. For example, in the environment with low illumination intensity, the processor 130 may change a transformation value regarding brightness, sharpness, contrast adjustment, noise removal, etc. and determine the transformation value as image transformation information.

Figure 10:
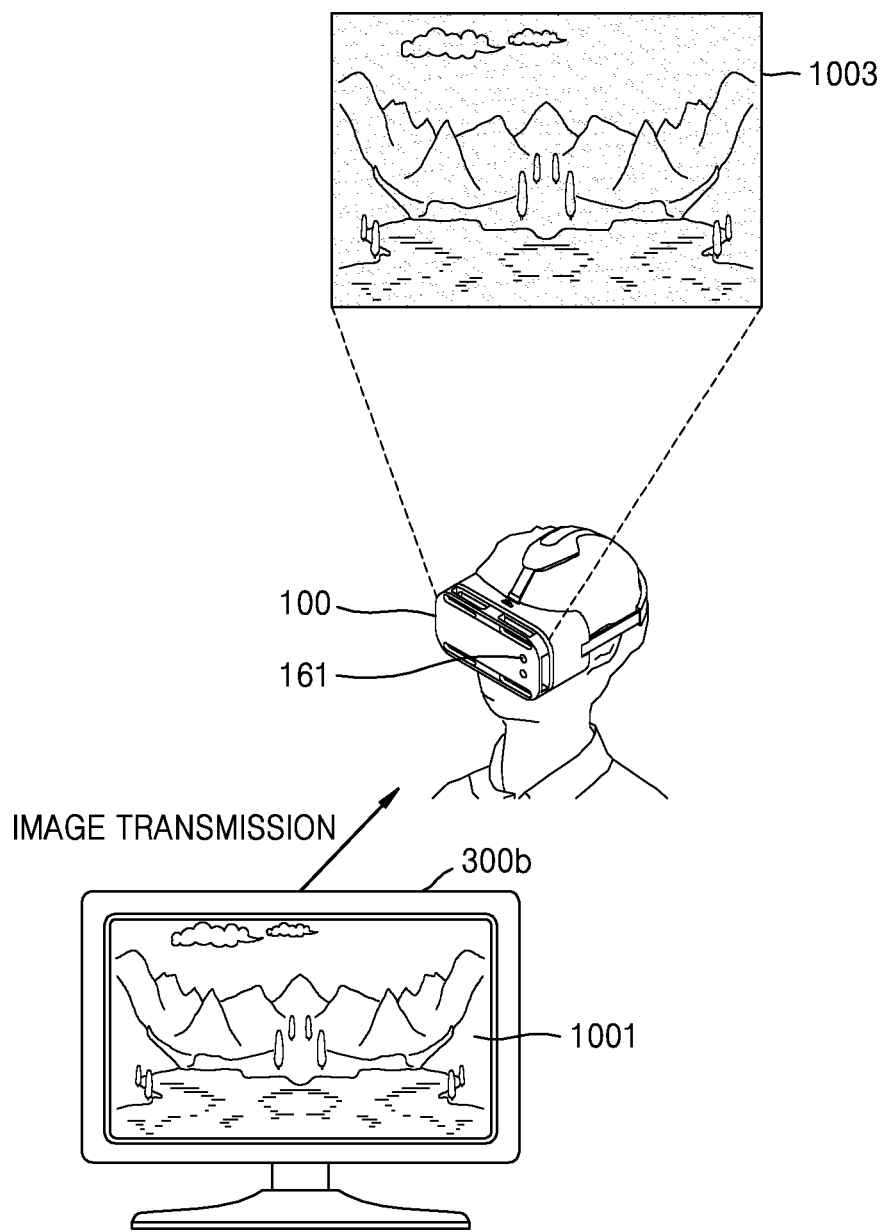
FIG. 10 is a diagram of an example of transforming and providing an image received from an external device.

FIG. 10 is a diagram of an example of transforming and providing an image received from an external device.

According to an aspect of an example embodiment, the display device 100 may receive image content that is being output by the external display device 300b from the external display device 300b. In this regard, the display device 100 may receive image content transformed based on visual condition information of a user. The image content may be a VR image but is not limited thereto.

The external display device 300b may receive image content from an external source via at least one of a high-definition multimedia interface (HDMI) port, a component jack, a Video Graphics Array (VGA) port, a DisplayPort, or a Universal Serial Bus (USB) port.

The external display device 300b may perform image transformation processing on image content so that the user with low vision may recognize the image content more clearly, and then, may transmit transformation-processed image content to the display device 100.

Figure 27:
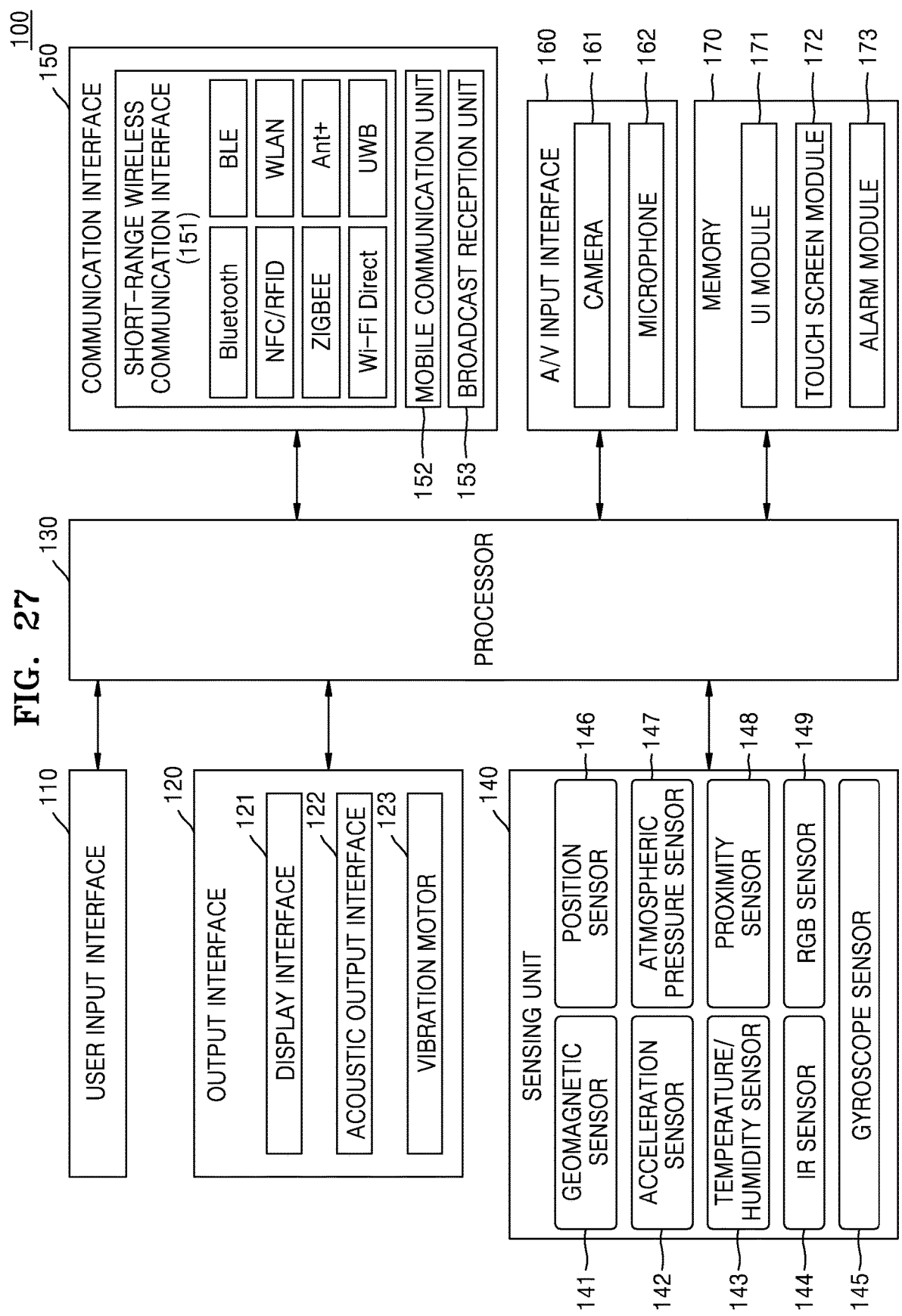

The display device 100 may receive image content via a communication interface (e.g., the communication interface 150 of FIG. 27). For example, the display device 100 may receive the image content through a wireless communication method such as IR, Bluetooth, Bluetooth low energy (BLE), ultrasound waves, Zigbee, and Wi-Fi.

In addition, the processor 130 of the display device 100 may receive image content and then transform the image, based on at least one of visual condition information of the user and image transformation information. The processor 130 may display a transformed image on the display 121.

FIGS. 4 to 10 illustrate one or more example embodiments but are not limited thereto.

Figure 11:
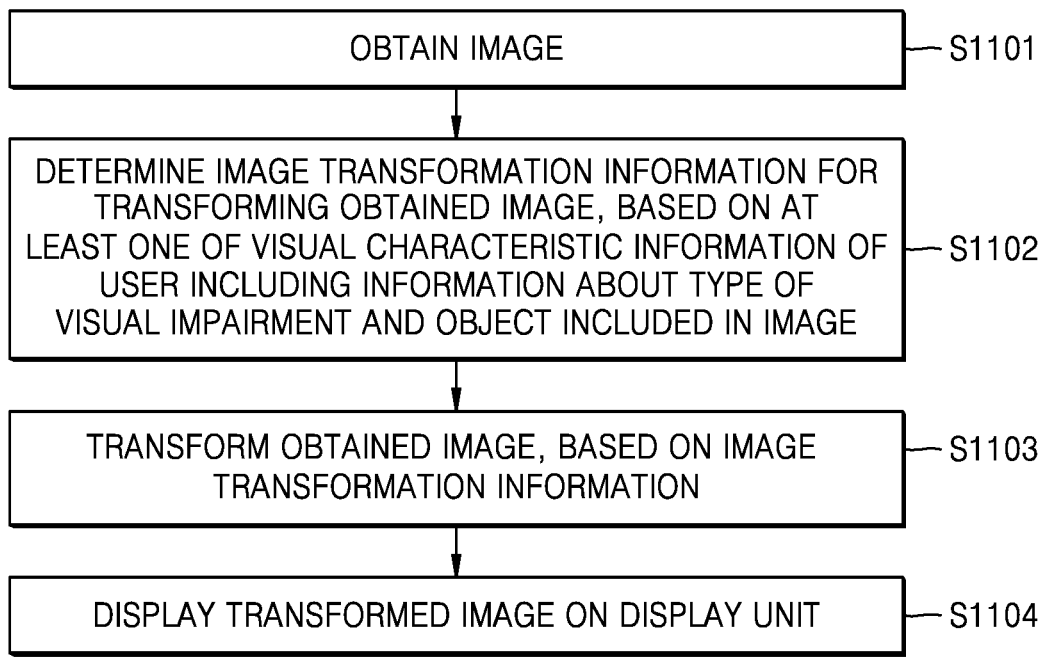
FIG. 11 is a flowchart of a method of operating a display device, according to an example embodiment.

FIG. 11 is a flowchart of a method of operating a display device according to an example embodiment. FIGS. 12 to 16 are diagrams of examples of providing an image transformed based on an object included in the image. FIG. 11 will be described with reference to the examples illustrated in FIGS. 12 to 16.

In operation S1101, the display device 100 may obtain an image to be displayed on the display 121.

The processor 130 may obtain an image captured by the camera 161, an image received from an external source via the communication interface 150, and/or an image stored in the memory 170 as an image to be displayed on the display 121.

In operation S1102, the display device 100 may determine image transformation information for transforming the obtained image, based on at least one of visual condition information of a user including a type of visual impairment and an object included in the image. In operation S1103, the display device 100 may transform the obtained image, based on the image transformation information. In operation S1104, the display device 100 may display a transformed image on the display 121.

The processor 130 may extract an object included in an image and may determine image transformation information, based on an attribute of the object.

For example, the object may be text, a person, a landscape, and/or a screen of another display device.

Figure 12:
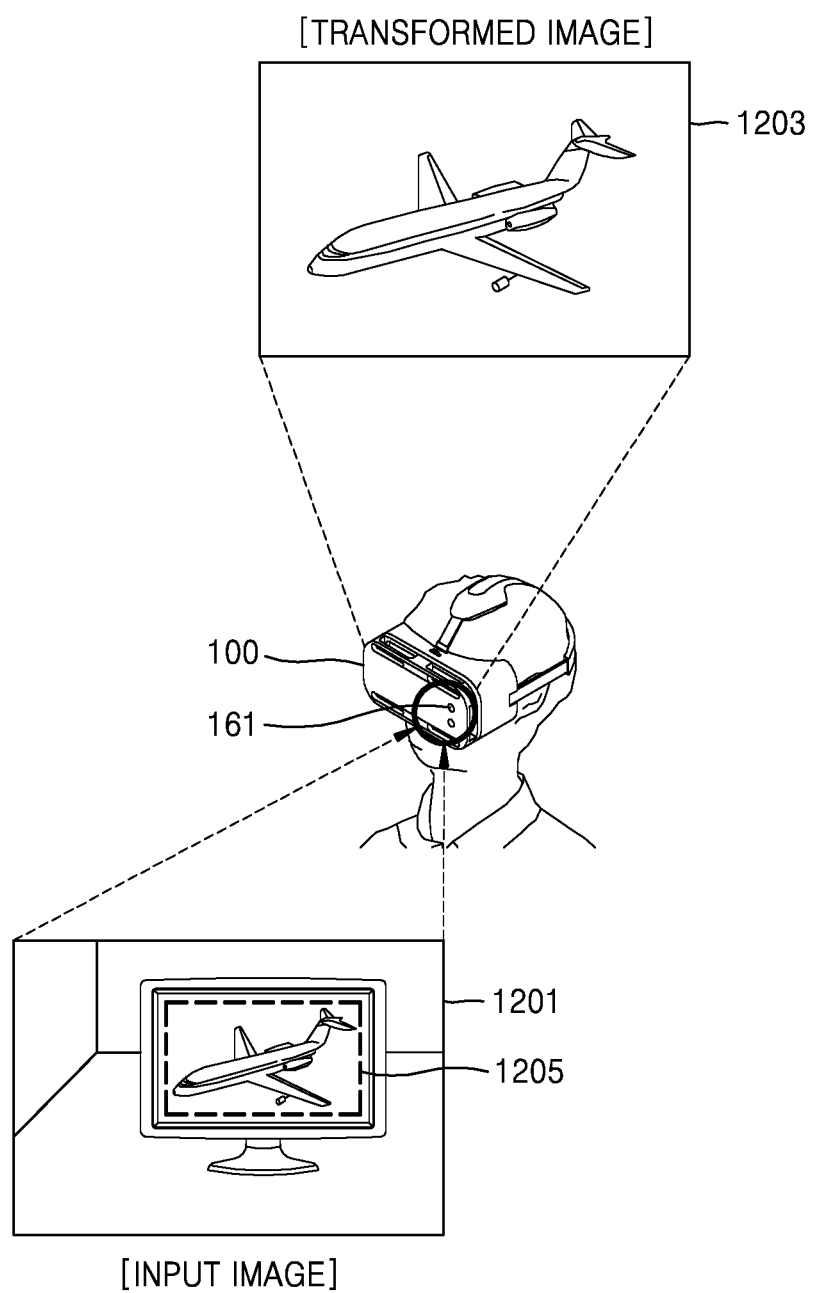
FIGS. 12 to 16 are diagrams of examples of providing an image transformed based on an object included in the image.

Referring to FIG. 12, according to an aspect of an example embodiment, the processor 130 may enlarge and display an image that is output by a screen of another display device.

The processor 130 may extract a screen 1205 of another display device in an input image 1201 captured by the camera 161. The processor 130 may determine a transformation value for enlarging and displaying an image in the screen 1205 as image transformation information.

The processor 130 may display an image 1203 obtained by enlarging only an image region of the screen 1205 on the display 121. For example, the display device 100 may allow a user watching TV to see via an entire region of the display 121 in full screen, only the image of the TV screen with the surrounding image cropped off, and thus, the user may have a highly immersive experience.

In addition, the processor 130 may determine image transformation information for transforming an image including a screen region except a surrounding image, based on visual condition information of a user (e.g., low vision, metamorphopsia, etc.).

Figure 13:
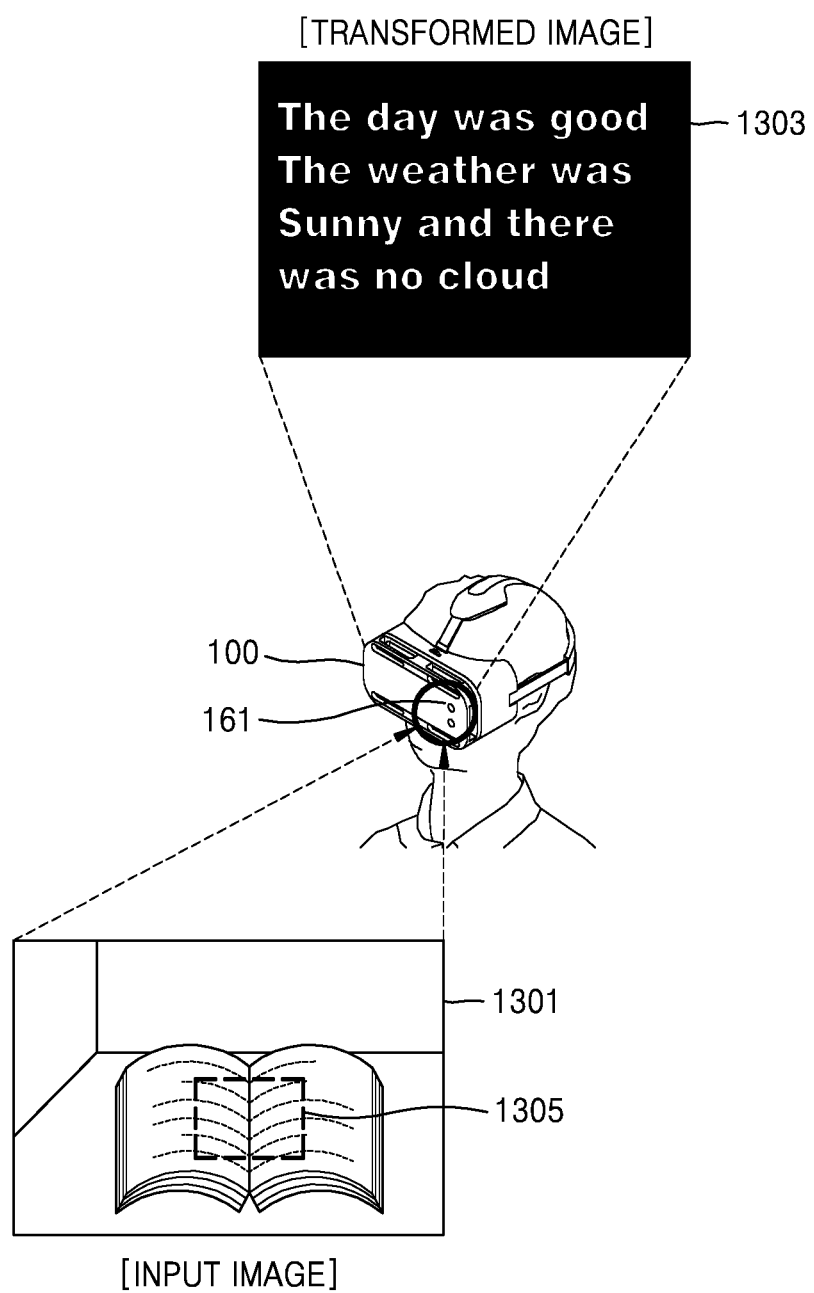

Referring to FIG. 13, according to an aspect of an example embodiment, the processor 130 may enlarge and display a text region of a book.

The processor 130 may extract an object including text of a book, a newspaper, or the like in an input image 1301. The processor 130 may determine image transformation information including a transformation value for extracting lines of text from a text region and enlarging and displaying the lines of text.

For example, when the display device 100 obtains an image 1301 that includes a book via the camera 161, the display device 100 may provide high readability to a user by enlarging and displaying only a text region 1305 of the book excluding a surrounding image.

In addition, the processor 130 may determine image transformation information for transforming an image 1303 including a text region excluding a surrounding image of a book, based on visual condition information of the user (e.g. low vision, myopia, hyperopia, metamorphopsia, etc.).

Figure 14:
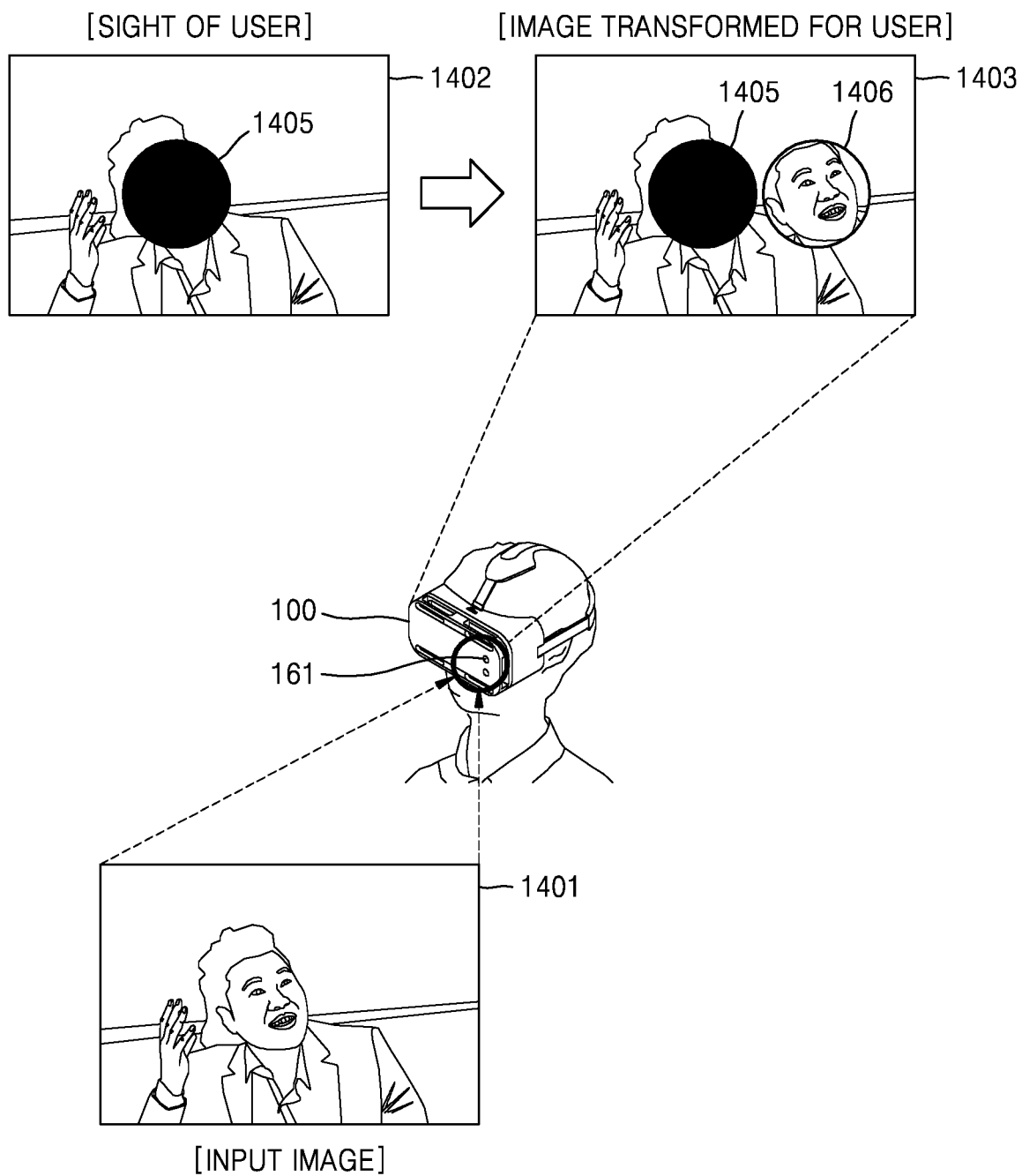

Referring to FIG. 14, according to an aspect of an example embodiment, the processor 130 may provide an image transformed to allow a user to recognize a person included in an image.

For example, vision of the user with a central scotoma symptom may perceive an image 1402 having a central region obscured, and accordingly, when the central region of the image includes a person, the user may not be able to identify the person.

The processor 130 may extract a face of a person in an input image 1401. In addition, the processor 130 may determine image transformation information, based on visual condition information of the user (e.g., a location, a size, and a shape of central scotoma).

For example, the processor 130 may determine image transformation information including a transformation value for changing a display location of a person's face obscured by a central scotoma region in an image and displaying the face.

Figure 15:
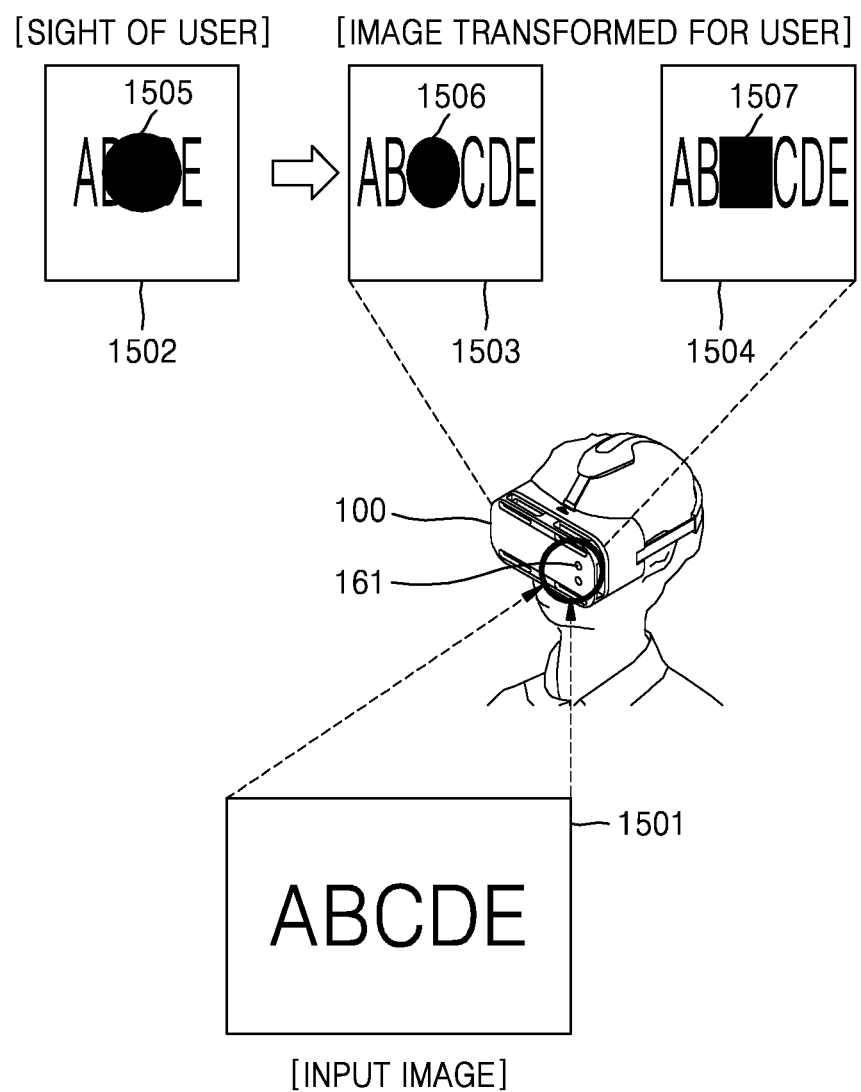

Referring to FIG. 15, according to an aspect of an example embodiment, the processor 130 may change a display location of text and display the text.

A portion of text may be obscured due to a central scotoma region 1505 in an image 1502 that is in the field of vision of a user with a central scotoma symptom.

The processor 130 may extract text in an input image 1501. In addition, when the processor 130 obtains a location, a size, and a shape of central scotoma as visual condition information of the user, the processor 130 may determine image transformation information for moving a display location of text to another region except the region affected by a central scotoma.

For example, the processor 130 may determine image transformation information for displaying text (e.g., letters "BCD") that is obscured due to the central scotoma region 1505 on left and right regions of the central scotoma region. The processor 130 may display an image 1503 or 1504 including a portion (e.g., letter "B") of text corresponding to the central scotoma region 1505 on a left region of the central scotoma region (1506, 1507) and may display another portion (e.g., letters "CD") of the text on a right region of the central scotoma region (1506, 1507). Also, on the image 1503 and 1504, the processor 130 may move a display location of text (e.g., letters "A" and "E") not to be obscured by the displayed text (e.g., letters "BCD"). For example, text (e.g., letters "AB") may be displayed on a left region of the central scotoma region 1506 and 1507, and text (e.g., letters "CDE") may be displayed on a right region of the central scotoma region 1506 and 1507.

The processor 130 may display a region corresponding to central scotoma of the user as having a circular shape 1506, a quadrilateral shape 1507, or the like in a transformed image but is not limited thereto.

Figure 16:
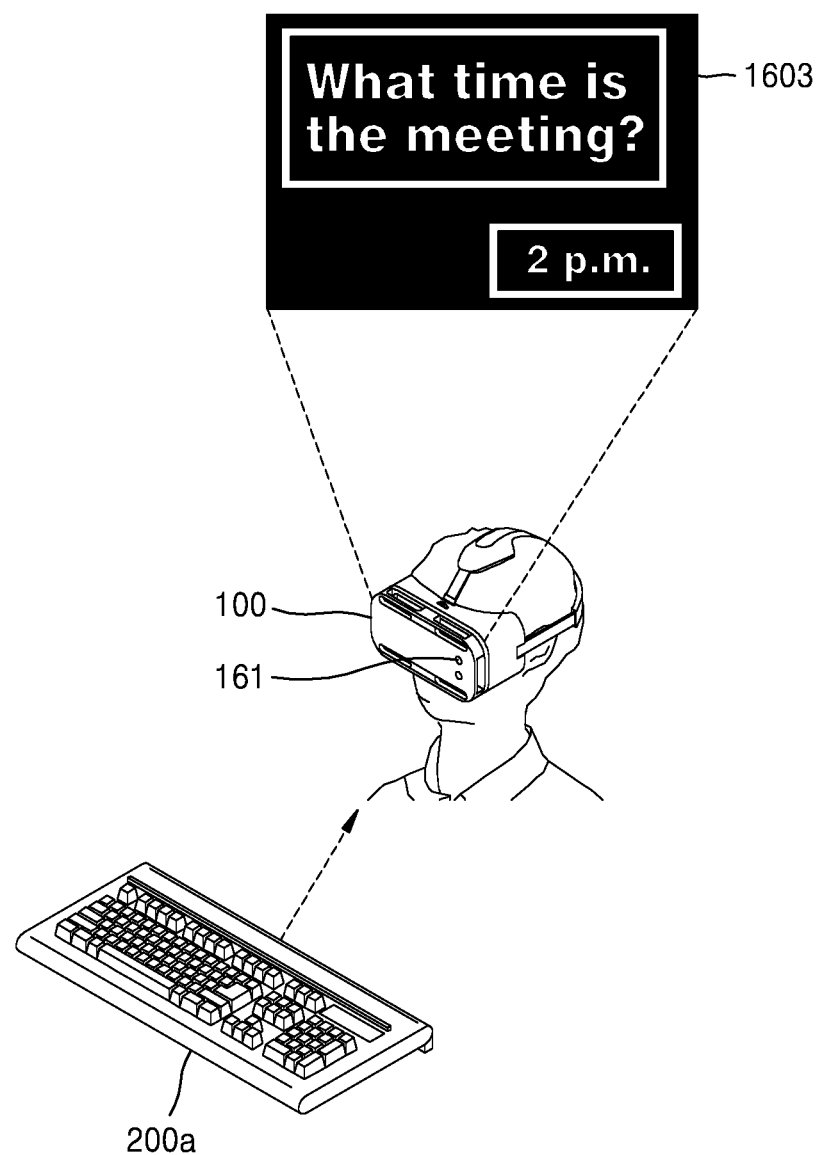

Referring to FIG. 16, according to an aspect of an example embodiment, the processor 130 may display text that is input via a keyboard 200*a* on the display 121.

The processor 130 may obtain text that is input via the keyboard 200*a* as an object to be displayed on the display 121, and may determine image transformation information for highlighting the text by using color inversion of lines of the text and background.

In addition, the processor 130 may determine image transformation information including a transformation value regarding an enlargement ratio of text and color inversion, based on visual condition information of a user (e.g., low vision, astigmatism, etc.).

Each of FIGS. 12 to 16 illustrates an example embodiment but is not limited thereto.

Figure 17:
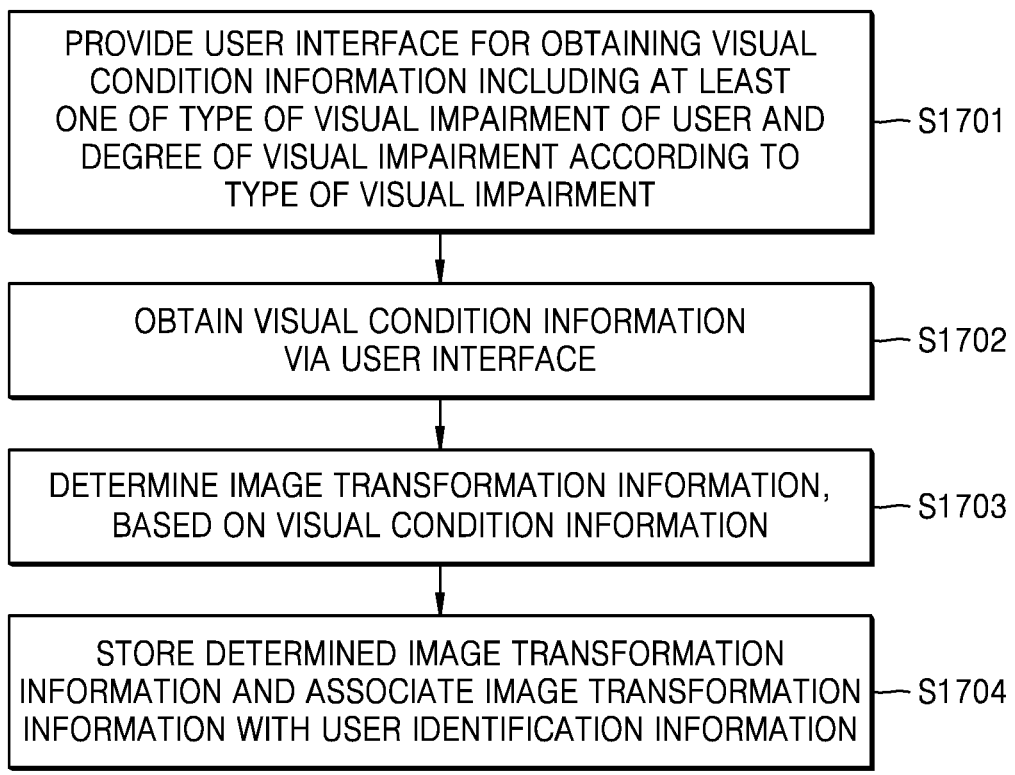
FIG. 17 is a flowchart of a method of determining image transformation information, according to an example embodiment.

FIG. 17 is a flowchart of a method of determining image transformation information according to an example embodiment. FIGS. 18 to 23 are diagrams of examples of determining image transformation information according to an example embodiment. FIG. 17 will be described with reference to the examples illustrated in FIGS. 18 to 23.

In operation S1701, the display device 100 may provide a user interface for obtaining visual condition information including at least one of a type of visual impairment of a user and a degree of visual impairment according to the type of visual impairment. In operation S1702, the display device 100 may obtain visual condition information via the user interface. In operation S1703, the display device 100 may determine image transformation information based on the visual condition information.

For example, when the user is sensed as wearing the display device 100 in the form of a headset, the display device 100 may display a user interface for receiving an input of visual condition information of the user on the display 121. The user may then be able to input the visual condition information through the user interface. In addition, for example, when a user input (e.g., pressing a button included in the display device 100) is received, the display device 100 may display a user interface for receiving an input of visual condition information of the user on the display 121 but is not limited thereto.

The display device 100 may output contents displayed on the display 121 as sound via an acoustic output interface (e.g., an acoustic output interface 122 of FIG. 27).

The display device 100 may receive input information via the control device 200 (e.g., the keyboard 200*a*, the remote control 200*b*). For example, the display device 100 may receive an input signal for selecting a selection item displayed on the display 121 by moving up and down and from side to side, via the remote control 200*b*.

Figure 18:
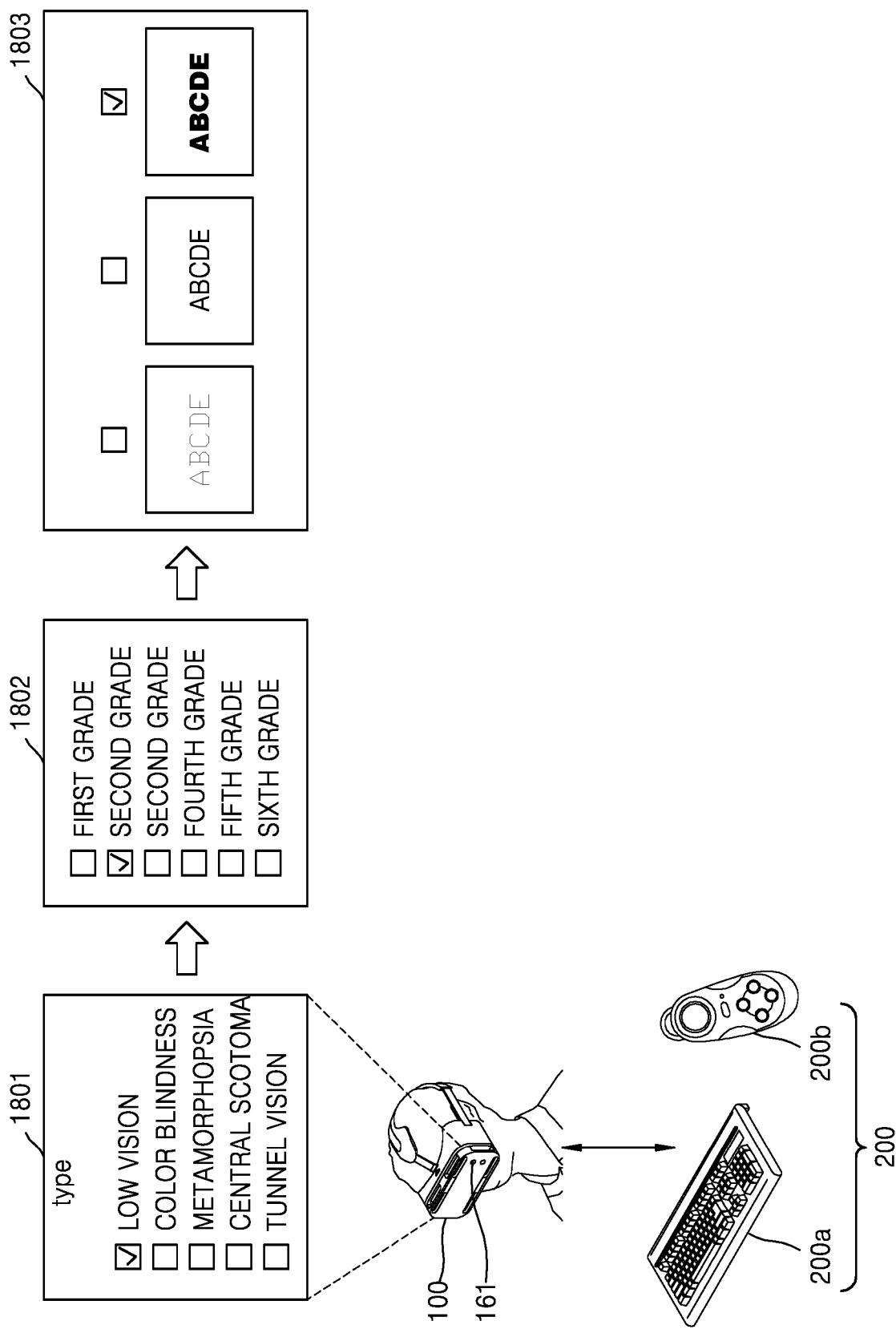
FIGS. 18 to 23 are diagrams of examples of determining image transformation information, according to an example embodiment.

FIG. 18 illustrates an example of obtaining visual condition information regarding low vision.

As illustrated in FIG. 18, the processor 130 may display types of visual impairment on the display 121 and may receive a user input for selecting low vision (1801). Also, the processor 130 may display different grades or levels of low vision on the display 121 and may receive a user input for selecting a visual impairment rating (e.g., a second grade) of a user (1802). For example, the grades may indicate the severity of visual impairment according to a predetermined measuring standard. Also, the processor 130 may provide examples of a transformation image on the display 121 and may receive a user input for selecting an image that is most visible to the user (1803).

The processor 130 may determine image transformation information, based on visual condition information (e.g., low vision, second grade, an image selected as the image most visible to the user) of the user input via a user interface.

Figure 19:
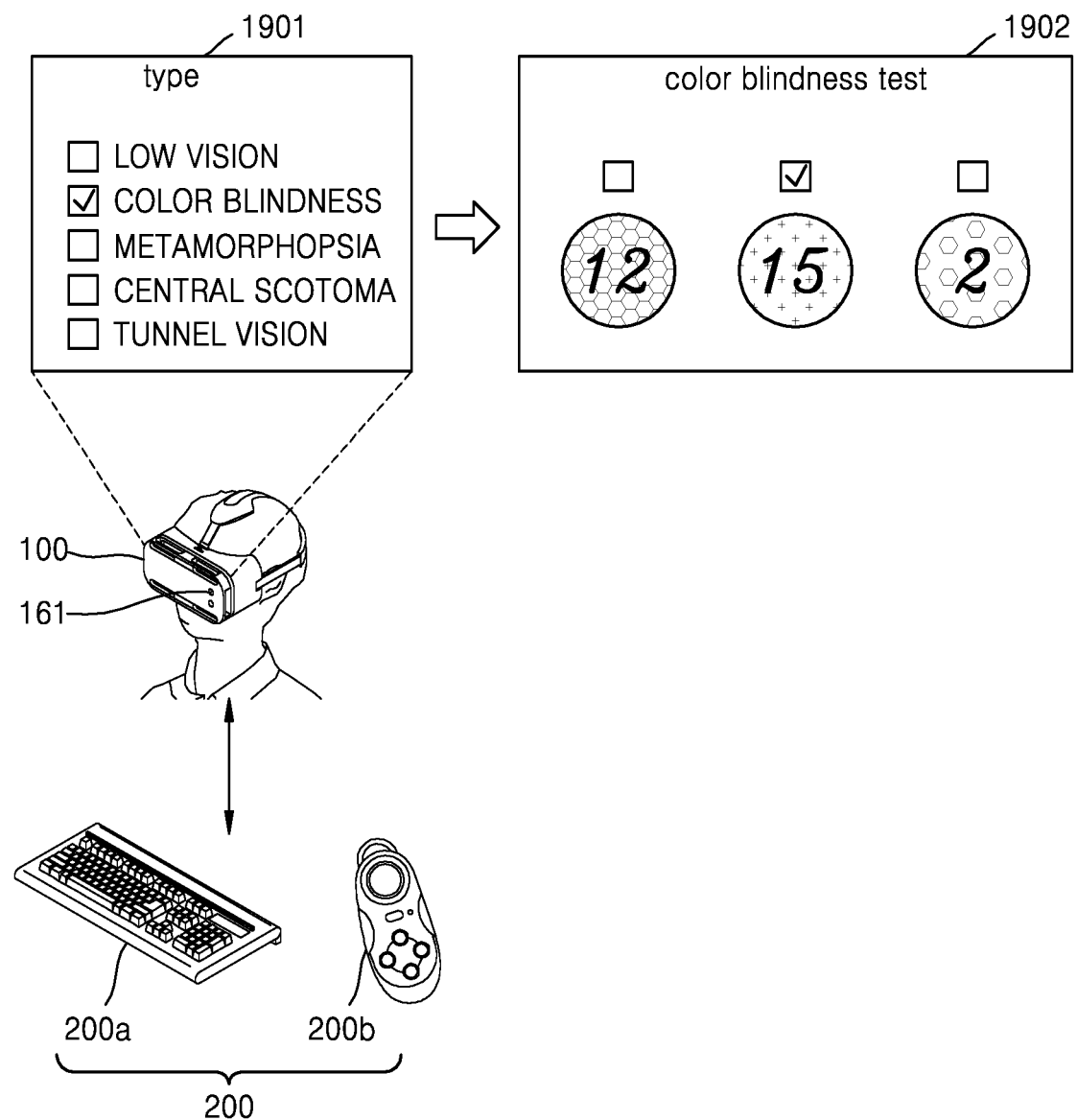

FIG. 19 illustrates an example of obtaining visual condition information regarding color blindness.

As illustrated in FIG. 19, the processor 130 may display types of visual impairment on the display 121 and may receive a user input for selecting color blindness (1901). Also, the processor 130 may display a test screen (e.g., Ishihara color vision test) for identifying a type of color blindness (e.g., red-green color blindness, blue-yellow color blindness, or total color blindness) on the display 121 (1902).

The processor 130 may determine image transformation information, based on visual condition information (e.g., red-green color blindness) of a user obtained via a user interface.

Figure 20:
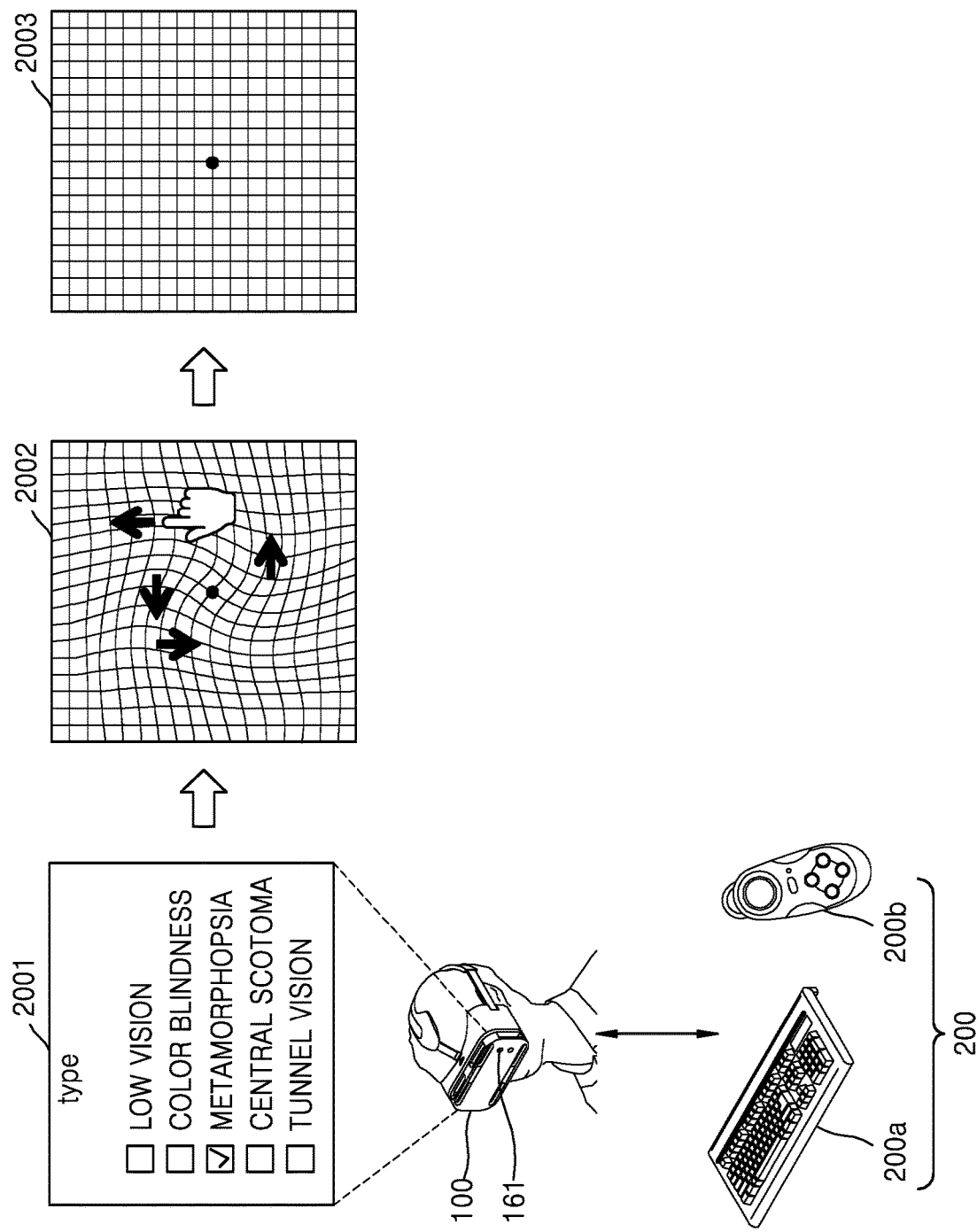

FIG. 20 illustrates an example of obtaining visual condition information regarding metamorphopsia.

As illustrated in FIG. 20, the processor 130 may display types of visual impairment on the display 121 and may receive a user input for selecting metamorphopsia (2001). Also, the processor 130 may display a grid test screen (e.g., an Amsler grid chart) for identifying a location that looks distorted to a user and a degree of distortion on the display 121.

The processor 130 may receive a user input for correcting lines that look distorted to the user into straight lines (2002). For example, the processor 130 may receive a user input for moving an icon displayed on the test screen from side to side and up and down via the keyboard 200*a* or the remote control 200*b*. The processor 130 may receive a user input for moving and adjusting the lines that look distorted until the lines look straight (2003).

The processor 130 may analyze an input correction pattern via a grid test and may determine image transformation information for correcting an image so that the image may not look distorted to the user, by inversely applying a correction pattern.

Figure 21:
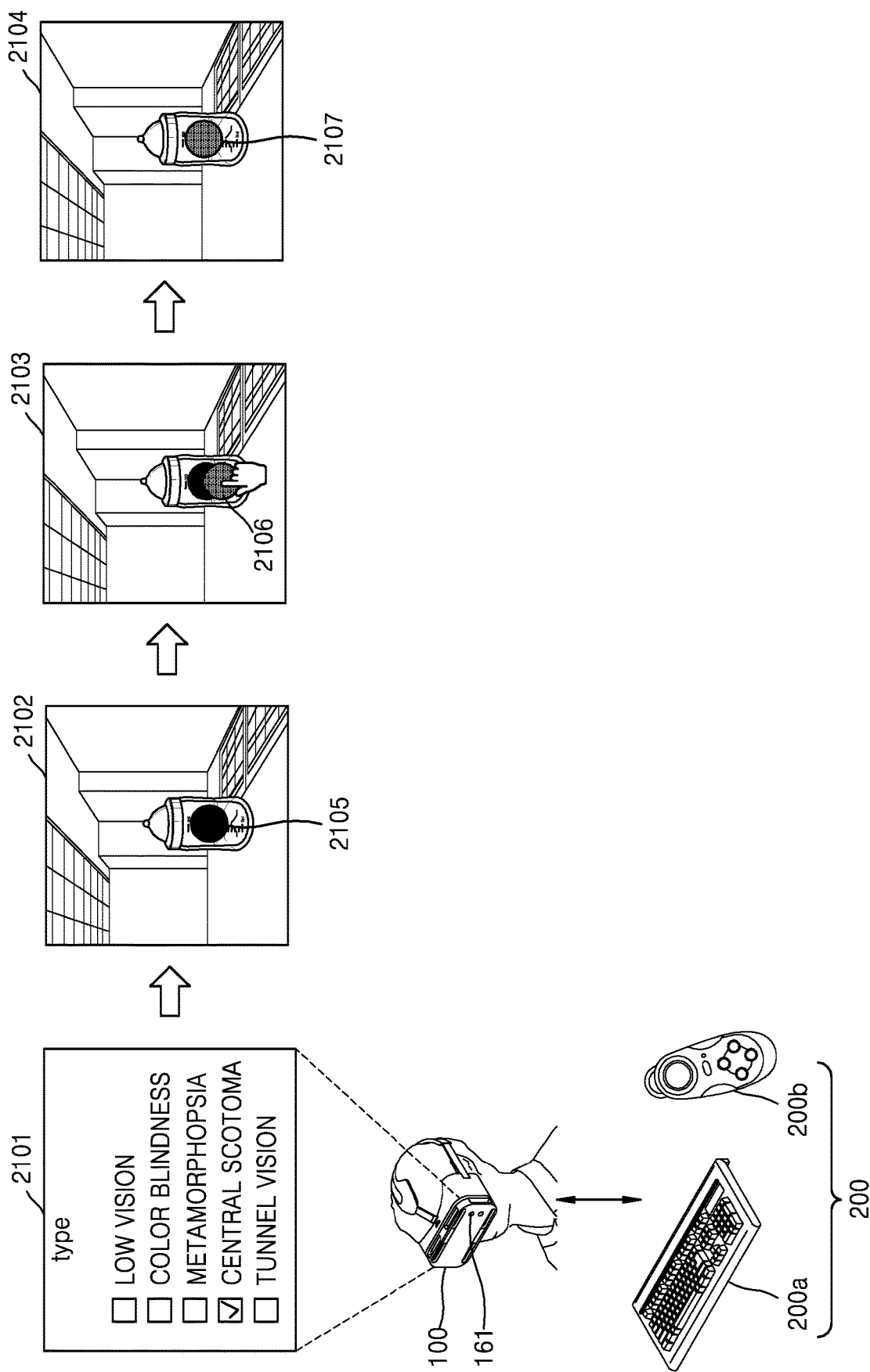
Figure 22:
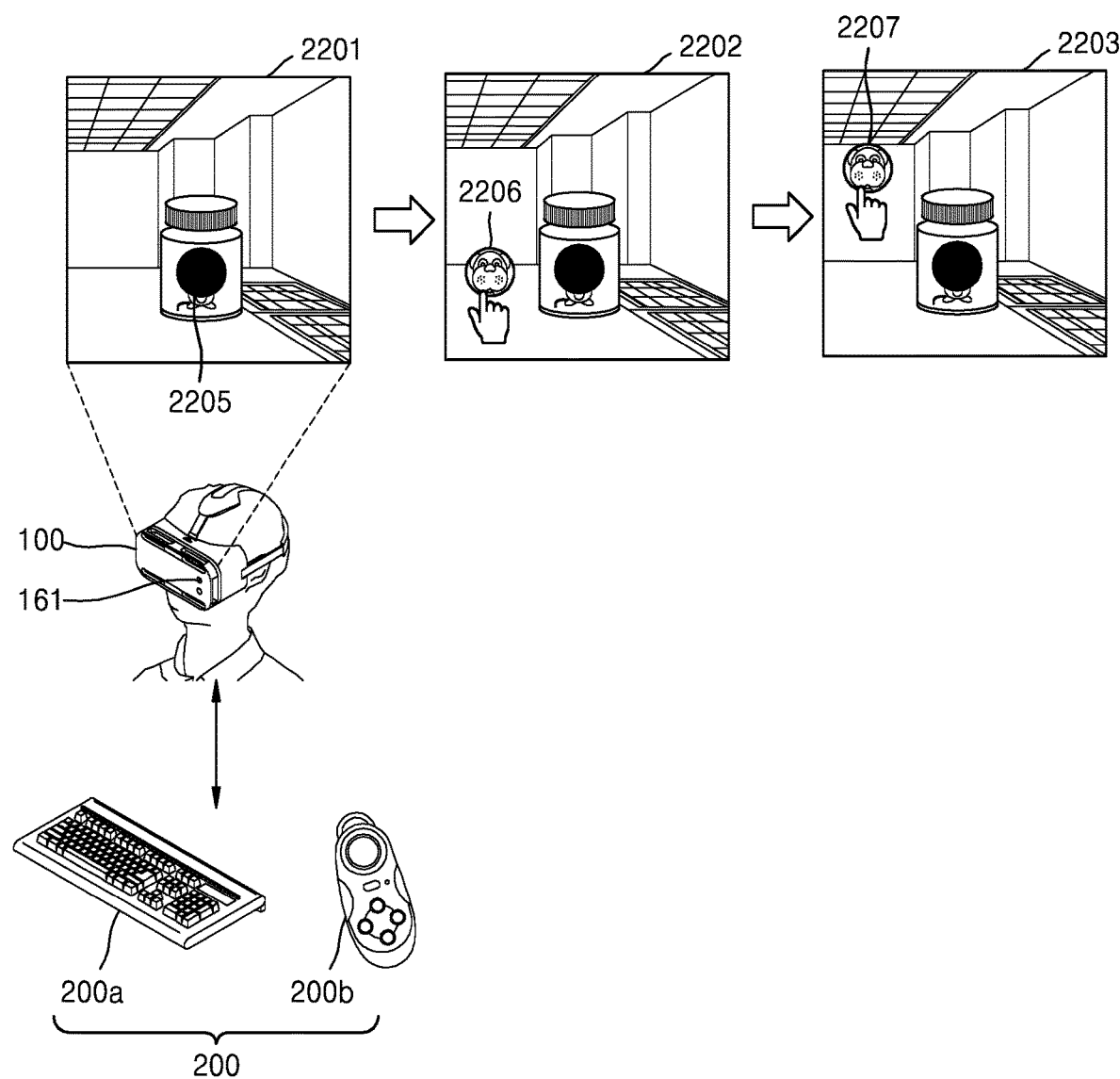

FIGS. 21 and 22 illustrate examples of obtaining visual condition information regarding a central scotoma symptom.

As illustrated in FIG. 21, the processor 130 may display types of visual impairment on the display 121 and may receive a user input for selecting central scotoma (2101). Also, the processor 130 may display a predetermined image 2102 (e.g., a sample image) on the display 121. In this regard, a central portion 2105 of the image 2102 may be partially obscured to a user with the central scotoma symptom.

The processor 130 may display an icon 2106 having a circular shape on the display 121 and may receive a user input for adjusting a location and size of the icon 2106. For example, the processor 130 may receive a user input for changing a location of the icon 2106, selecting a shape (e.g., a circular shape, an oval shape, a quadrilateral shape, a racket shape, etc.) of the icon 2106, or increasing or decreasing a size of the icon 2106, via a button input of the remote control 200*b* (2103).

The processor 130 may receive a user input for adjusting a location, a size, and a shape of an icon 2107 until a central scotoma region of the user is completely included (2104). For example, the processor 130 may receive a user input for increasing a size of the icon 2107 to completely cover a region of central scotoma of the user.

The processor 130 may determine a central scotoma region of the user via a user input, and may determine image transformation information based on the determined central scotoma region.

Referring to FIG. 22, the processor 130 of the display device 100 may receive a user input for selecting a location of where a replacement image corresponding to a central scotoma region is to be displayed by moving the image.

The processor 130 may display a predetermined image (e.g., a sample image) on the display 121 (2201). In this regard, a portion 2205 of a central portion of the image may be invisible to a user with a central scotoma symptom (2201).

The processor 130 may display an icon 2206 on the display 121 and may receive a user input for adjusting a location and size of the icon 2206 having a circular shape (2202).

For example, the processor 130 may receive a user input for changing a location of the icon 2206, via a button input of the keyboard 200*a* or the remote control 200*b*. The processor 130 may determine a location where an image corresponding to a scotoma region of the user is to be displayed by moving the replacement image, based on a user input for adjusting a location and a size of the icon 2206.

Also, the processor 130 may change a location where a replacement image corresponding to a scotoma region of the user is to be displayed, according to a user input for moving an icon 2207 up and down and from side to side (2203). Thus, the user may be able to view the portion of the image obscured by the scotoma region at a new location designated by the icon 2207.

Figure 23:
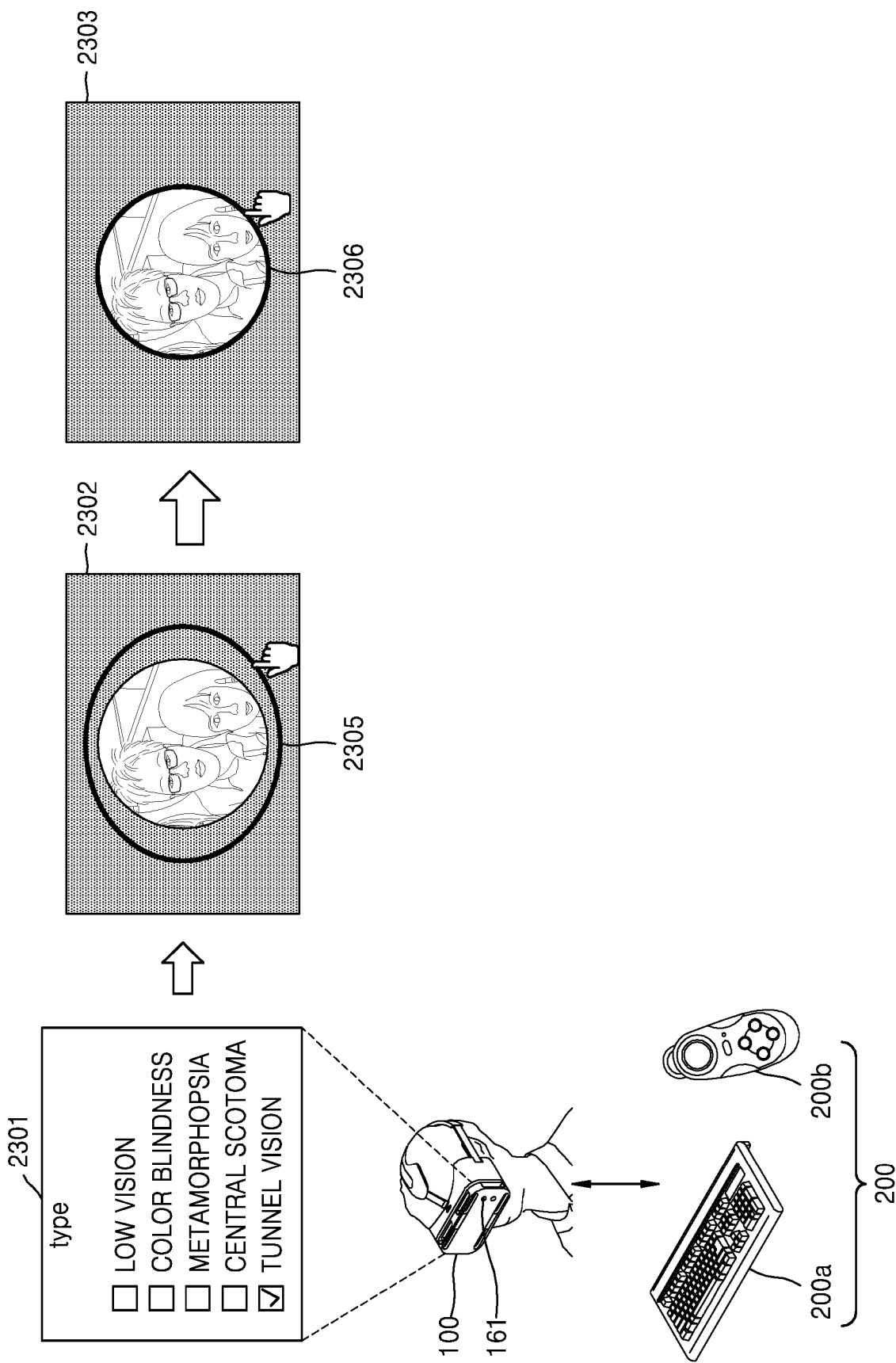

FIG. 23 illustrates an example of obtaining visual condition information regarding a tunnel vision symptom.

As illustrated in FIG. 23, the processor 130 may display types of visual impairment on the display 121 and may receive a user input for selecting tunnel vision (2301). Also, the processor 130 may display a predetermined image (e.g., a sample image) on the display 121 (2302). In this regard, a peripheral portion of the image may be partially invisible to a user with the tunnel vision symptom (2302).

The processor 130 may display an icon 2305 having a circular or oval shape on the display 121 and may receive a user input for adjusting a location and a size of the icon 2305. For example, the processor 130 may increase or decrease a size of the icon 2305 having a circular shape, via a button input of the keyboard 200*a* or the remote control 200*b* (2302).

The processor 130 may receive a user input for adjusting a location, a size, and/or a shape of an icon 2306 until the icon 2306 matches a boundary of a region that is obscured due to tunnel vision of the user (2303).

The processor 130 may determine a tunnel vision region of the user via a user input. Based on the determined tunnel vision region, the processor 130 may determine image transformation information for reducing and displaying an entire image within the tunnel vision region.

In operation S1704 of FIG. 17, the display device 100 may store the determined image transformation information and associate the image transformation information with user identification information of the user.

The user identification information may be information for distinguishing a plurality of users. For example, the user identification information may be a number, a letter, a symbol, a certain key input signal, etc. but is not limited thereto. The user identification information may be a name, a username, an identification number, a serial number, a nickname, etc.

The display device 100 may store image transformation information corresponding to user identification information for each user in the memory 170.

The processor 130 of the display device 100 may extract image transformation information corresponding to user identification information from among image transformation information for a plurality of users stored in the memory 170.

For example, the processor 130 may extract image transformation information corresponding to user identification information, based on an input (e.g., a user input using a certain button, etc. of the control device 200 or the display device 100) that is set in response to the user identification information, and may display an image transformed based on the extracted image transformation information.

In addition, the processor 130 may store visual condition information of a user in the memory 170 so as to correspond to user identification information. The processor 130 may store visual condition information respectively corresponding to user identification information for one or more users in the memory 170.

In addition, the processor 130 may transform an input image by using image transformation information and/or visual condition information corresponding to user identification information stored in the memory 170.

FIGS. 18 to 23 illustrate examples of displaying a user interface on the display 121 but are not limited thereto. For example, the display device 100 may output audio instructions via the acoustic output interface 122 so that a user may input visual condition information, and may receive an input of visual condition information of the user via the control device 200 (e.g., the keyboard 200a, the remote control 200b).

Each of FIGS. 18 to 23 illustrates an example embodiment but is not limited thereto.

Figure 24:
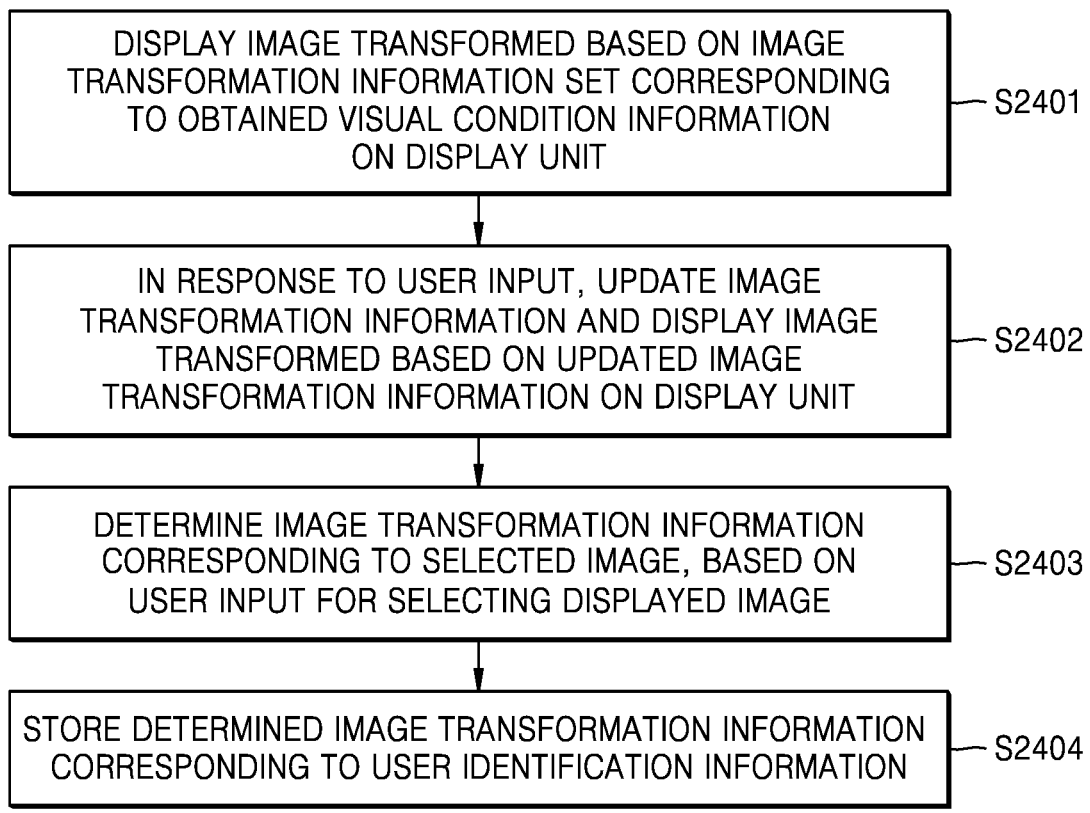
FIG. 24 is a flowchart of a method of determining image transformation information, according to an example embodiment.

FIG. 24 is a flowchart of a method of determining image transformation information according to another embodiment.

In operation S2401, the display device 100 according to an aspect of an example embodiment may display an image transformed based on image transformation information that is set in response to obtained visual condition information on the display 121.

The processor 130 of the display device 100 may determine image transformation information that is set as a default in response to visual condition information. The memory 170 of the display device 100 may have previously stored a transformation value for transforming an image based on visual condition information. In addition, the display device 100 may receive image transformation information corresponding to visual condition information from the external device 300.

For example, the display device 100 may have previously set an average transformation value (e.g., a zoom ratio of an image, a contrast adjustment ratio of outline, etc.) for transforming an image with respect to low vision.

In operation S2402, according to a user input, the display device 100 may update the image transformation information and may display an image transformed based on the updated image transformation information on the display 121.

The processor 130 may receive a user input for updating image transformation information. For example, the processor 130 may update image transformation information, based on a user input for manipulating a button included in the display device 100, and may transform an image based on the updated image transformation information. In addition, the processor 130 may update image transformation information, based on a control signal via the remote control 200b, but is not limited thereto.

The display device 100 may display an image transformed based on the updated image transformation information on the display 121.

In operation S2403, based on a user input for selecting a displayed image, the display device 100 may determine image transformation information corresponding to a selected image.

The processor 130 of the display device 100 may provide an image that is transformed in response to a user input to the display 121, and may receive an input for selecting a transformed image that is clearly visible to a user. For example, the processor 130 may receive a user input for selecting a transformed image by using a button, etc. included in the display device 100 or the control device 200.

The processor 130 may determine image transformation information corresponding to a transformed image selected by a user input.

In operation S2404, the display device 100 may store the determined image transformation information so that the image transformation information is associated with (e.g., corresponds to) user identification information.

The processor 130 may store image transformation information corresponding to a selected transformation image in the memory 170 so that the image transformation information corresponds to user identification information.

In addition, the processor 130 may store a plurality of pieces of image transformation information (e.g., a plurality of image transformation values) so as to respectively correspond to a plurality of pieces of user identification information (e.g., a plurality of users). The processor 130 may access image transformation information stored in the memory 170 based on user identification information.

Figure 25:
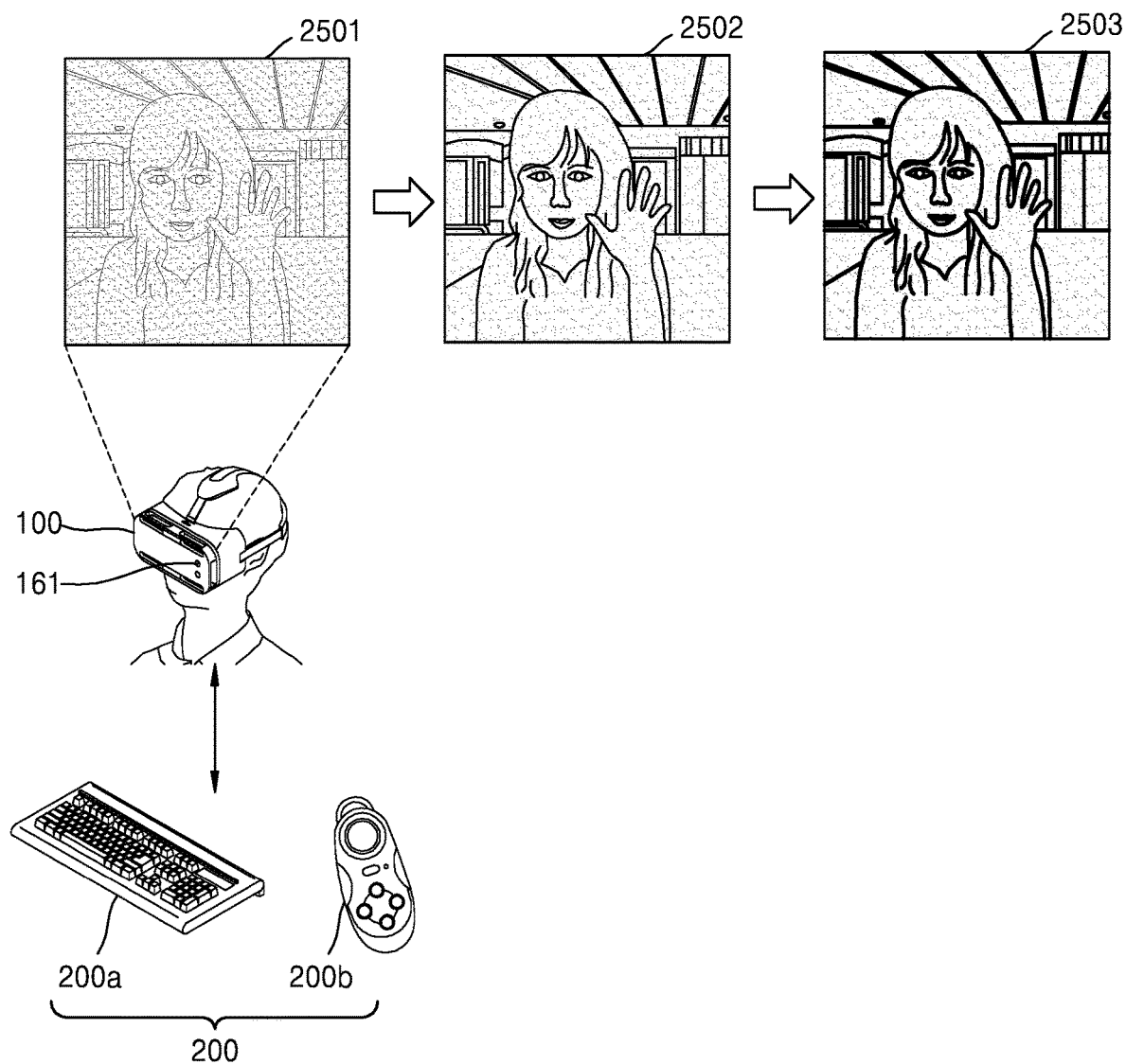
FIG. 25 is a diagram of an example of determining image transformation information, according to an example embodiment.

FIG. 25 is a diagram of an example of determining image transformation information according to an example embodiment.

As the display device 100 provides transformed images to the display 121, a user may select an optimum image (e.g., an image that best suits the user's visual needs).

Referring to FIG. 25, as the processor 130 of the display device 100 updates image transformation information based on a user input, the processor 130 may transform an image based on the updated image transformation information and may sequentially display transformed images 2501, 2502, and 2503.

The processor 130 may store image transformation information corresponding to an image selected by the user from among the plurality of transformed images 2501, 2502, and 2503, and associate the image transformation information with the user identification information of the user. For example, the user may select an image transformed based on the updated image transformation information via the display 121, by using a button, etc. included in the display device 100 or the control device 200. The processor 130 of the display device 100 may store image transformation information corresponding to a transformation image selected according to a user input.

FIG. 25 illustrates an example embodiment but is not limited thereto.

FIGS. 26 and 27 are block diagrams of a display device according to an example embodiment.

As illustrated in FIG. 26, the display device 100 may include the processor 130 and the display 121. However, not all of the elements illustrated in FIG. 26 are essential elements of the display device 100. The display device 100 may be implemented by more or fewer elements than the elements illustrated in FIG. 26.

For example, as illustrated in FIG. 27, the display device 100 may further include, in addition to the processor 130 and the display 121, a user input interface 110, an output interface 120, a sensing unit 140, the communication interface 150, an audio/video (A/V) input interface 160, and the memory 170. However, one or more of these components may be omitted or replaced by a different component.

The user input interface 110 may refer to a means via which a user inputs data for controlling the display device 100. For example, the user input interface 110 may include a keypad, a dome switch, a touch pad (e.g., a capacitive overlay touch pad, a resistive overlay touch pad, an IR beam touch pad, a surface acoustic wave touch pad, an integral strain gauge touch pad, a piezoelectric touch pad, or the like), a jog wheel, a jog switch, and the like, but is not limited thereto.

The user input interface 110 may receive a user input for setting visual condition information and image transformation information. In addition, the user input interface 110 may receive a user input for selecting a transformed image, in order to determine image transformation information.

The output interface 120 may output an audio signal, a video signal, or a vibration signal, and may include the display 121, the acoustic output interface 122 (e.g., a speaker), and a vibration motor 123.

The display 121 may display information processed by the display device 100. For example, the display 121 may display a user interface for receiving an input of visual condition information of the user, a user interface for setting image transformation information, and an image transformed based on image transformation information.

When the display 121 and a touch pad form a layer structure to configure a touchscreen, the display 121 may be used as not only an output device but also an input device. The display 121 may include a liquid crystal display (LCD), a thin film transistor liquid crystal display (TFT-LCD), an organic light-emitting diode (OLED), a flexible display, a 3D display, and/or an electrophoretic display. The display device 100 may include two or more display 121 according to an implementation form of the display device 100. In this regard, the two or more display 121 may be disposed to face each other by using a hinge.

The acoustic output interface 122 may output audio data received from the communication interface 150 or stored in the memory 170. In addition, the acoustic output interface 122 may output an acoustic signal related to a function (e.g., a call signal reception sound, a message reception sound, or an alarm sound) performed by the display device 100. The acoustic output interface 122 may be a speaker, a buzzer, or the like.

The acoustic output interface 122 may output an audio instruction for receiving an input of visual condition information and image transformation information. In addition, when the display device 100 reproduces image content, the acoustic output interface 122 may output audio data included in the image content.

The vibration motor 123 may output a vibration signal. For example, the vibration motor 123 may output a vibration signal corresponding to an output of audio data or video data (e.g., a call signal reception sound or a message reception sound). In addition, the vibration motor 123 may output a vibration signal when a touch is input via the touchscreen.

The processor 130 may control and oversee the general operations of the display device 100. For example, the processor 130 may control the user input interface 110, the output interface 120, the sensing unit 140, the communication interface 150, the A/V input interface 160, and the like by executing programs (e.g., instructions) stored in the memory 170. In addition, the processor 130 may perform functions of the display device 100 described with reference to FIGS. 1 to 25 by executing programs stored in the memory 170.

The processor 130 may be a graphics processing unit (GPU) for processing graphics data corresponding to video. The processor 130 may be implemented as a system on chip (SoC) that integrates a core and a GPU. The processor 130 may include a single core, a dual core, a triple core, a quad core, and a multiple core thereof.

In addition, the processor 130 may include a plurality of processors. For example, the processor 130 may be implemented as a main processor and a sub processor that operates in a sleep mode (e.g., low-power mode).

The GPU may generate a screen including various objects such as an icon, an image, and text by using an operation unit and a rendering unit. The operation unit may calculate an attribute value such as a coordinate value, a shape, a size, and a color where each object is to be displayed according to a layout of a screen by using a user input received via the user input interface 110. The rendering unit may generate a screen of various layouts including an object based on the attribute value calculated by the operation unit. The screen generated by the rendering unit may be displayed within a display region of the display 121.

The processor 130 may obtain an image. The processor 130 may obtain an image captured by the camera 161, an image received from an external device via the communication interface 150, and/or an image stored in the memory 170.

In addition, the processor 130 may determine image transformation information for transforming an obtained image, based on visual condition information of the user including a type of visual impairment.

The processor 130 may provide a user interface for obtaining visual condition information including a type of visual impairment of the user and/or a degree of visual impairment according to the type of visual impairment. The processor 130 may obtain visual condition information via the user interface, and determine image transformation information, based on the obtained visual condition information.

The processor 130 may control image transformation information to be stored in the memory 170 so as to correspond to user identification information.

The processor 130 may determine image transformation information, based on an object included in an obtained image. The object may include text, a person, a landscape, and/or a screen of another display device.

According to a user input, the processor 130 may change (i.e., update) image transformation information and may transform an image based on the updated image transformation information. The processor 130 may display a transformed image on the display 121 and may determine image transformation information corresponding to a selected image, based on a user input for selecting a displayed image.

The processor 130 may control image transformation information to be stored in the memory 170 so as to correspond to user identification information. The image transformation information may include a transformation value regarding change of a display location of an object included in an image, enlargement or reduction of an object, change of color and chroma of an object, and/or contrast change of outline of an object.

The processor 130 may transform an obtained image based on determined image transformation information and may display a transformed image on the display 121.

The sensing unit 140 may detect a state of the display device 100 or an ambient state of the display device 100 and may transmit detected information to the processor 130.

The sensing unit 140 may include a geomagnetic sensor 141, an acceleration sensor 142, a temperature/humidity sensor 143, an IR sensor 144, a gyroscope sensor 145, a position sensor (e.g., global positioning system (GPS)) 146, an atmospheric pressure sensor 147, a proximity sensor 148, and/or an RGB (illuminance) sensor 149, but is not limited thereto. A function and structure of each sensor are well-understood by those of ordinary skill in the art, and thus, a detailed description thereof is omitted herein.

The communication interface 150 may include one or more elements for communication between the display device 100 and the control device 200 or between the display device 100 and the external device (e.g., a server) 300. For example, the communication interface 150 may include a short-range wireless communication interface 151, a mobile communication interface 152, and a broadcast reception unit 153. Each module included in the communication interface 150 may be a communicator, a receiver, a transmitter, a transceiver, a network adapter, and/or a network interface.

The short-range wireless communication interface 151 may include a Bluetooth communication interface, a BLE communication interface, a near-field communication interface, a wireless local area network (WLAN) (Wi-Fi) communication interface, a Zigbee communication interface, an infrared data association (IrDA) communication interface, a Wi-Fi Direct (WFD) communication interface, an ultra-wideband (UWB) communication interface, an Ant+ communication interface, and the like but is not limited thereto.

The mobile communication interface 152 may transmit and receive a wireless signal to and from at least one of a base station, an external terminal, and a server in a mobile communication network. In this regard, the wireless signal may include a voice call signal, a video call signal, or various types of data according to text/multimedia message transmission and reception.

The broadcast reception unit 153 may receive a broadcast signal and/or broadcast related information from the outside via a broadcast channel. The broadcast channel may include a satellite channel and a terrestrial channel. According to an implementation example, the display device 100 may not include the broadcast reception unit 153.

In addition, the communication interface 150 may transmit and receive information required to transform an image based on visual condition information of the user and provide a transformed image to the display 121 to and from the control device 200 and the external device 300.

The A/V input interface 160 may receive an input of an audio signal or a video signal and may include the camera 161, a microphone 162, and the like. The camera 161 may obtain an image frame such as a still image, a moving picture, or the like via an image sensor in a video call mode or an image capturing mode. An image captured by the image sensor may be processed by the processor 130 or a separate image processing unit.

The image frame processed by the camera 161 may be stored in the memory 170 or may be externally transmitted via the communication interface 150. Two or more cameras 161 may be provided according to configuration of a terminal.

The microphone 162 may receive an external acoustic signal and process the external acoustic signal to electrical voice data. For example, the microphone 162 may receive an acoustic signal from an external device or a speaker. The microphone 162 may use various noise cancellation algorithms to cancel noise generated during a process of receiving an external acoustic signal.

The memory 170 may store a program for processing and control of the processor 130 and may store data that is input to the display device 100 or is output from the display device 100.

The memory 170 may include at least one type of storage medium from among a flash memory type memory, a hard disk type memory, a multimedia card micro type memory, a card type memory (e.g., a secure digital (SD) or extreme digital (XD) memory), random access memory (RAM), static RAM (SRAM), read-only memory (ROM), electrically erasable programmable ROM (EEPROM), programmable ROM (PROM), a magnetic memory, a magnetic disc, and an optical disc.

The programs stored in the memory 170 may be classified into a plurality of modules according to functions thereof, for example, into a user interface (UI) module 171, a touchscreen module 172, an alarm module 173, and the like.

The UI module 171 may provide a specialized UI, a specialized graphical user interface (GUI), or the like inter-operating with the display device 100 for each application. The touchscreen module 172 may sense a touch gesture of the user on the touchscreen and may transmit information regarding the touch gesture to the processor 130. The touchscreen module 172 may recognize and analyze a touch code. The touchscreen module 172 may be configured as separate hardware including a controller.

Various sensors may be provided inside or near the touchscreen to sense a touch or a proximity touch on the touchscreen. An example of a sensor for sensing a touch on the touchscreen is a tactile sensor. The tactile sensor is a sensor for sensing a contact of a certain object at a degree of human feeling or more. The tactile sensor may sense various pieces of information such as roughness of a contact surface, hardness of a contact object, a temperature of a contact point, and the like.

Another example of a sensor for sensing a touch on the touchscreen is a proximity sensor.

The proximity sensor is a sensor for detecting a presence of an object approaching a predetermined detection surface or a nearby object by using an electromagnetic force or an IR ray without a mechanical contact. Examples of the proximity sensor may include a transmissive optoelectric sensor, a direct reflective optoelectric sensor, a mirror reflective optoelectric sensor, a high-frequency oscillation proximity sensor, a capacitive proximity sensor, a magnetic proximity sensor, and an IR proximity sensor. Examples of a touch gesture of the user may include a tap, a touch & hold, a double tap, a drag, a pan, a flick, a drag & drop, and a swipe.

The alarm module 173 may generate a signal for notifying an occurrence of an event of the display device 100.

Examples of an event that occurs in the display device 100 may include call signal reception, message reception, key signal input, and schedule notification. The alarm module 173 may output an alarm signal in the form of a video signal via the display 121, may output an alarm signal in the form of an audio signal via the acoustic output interface 122, or may output an alarm signal in the form of a vibration signal via the vibration motor 123.

Figure 28:
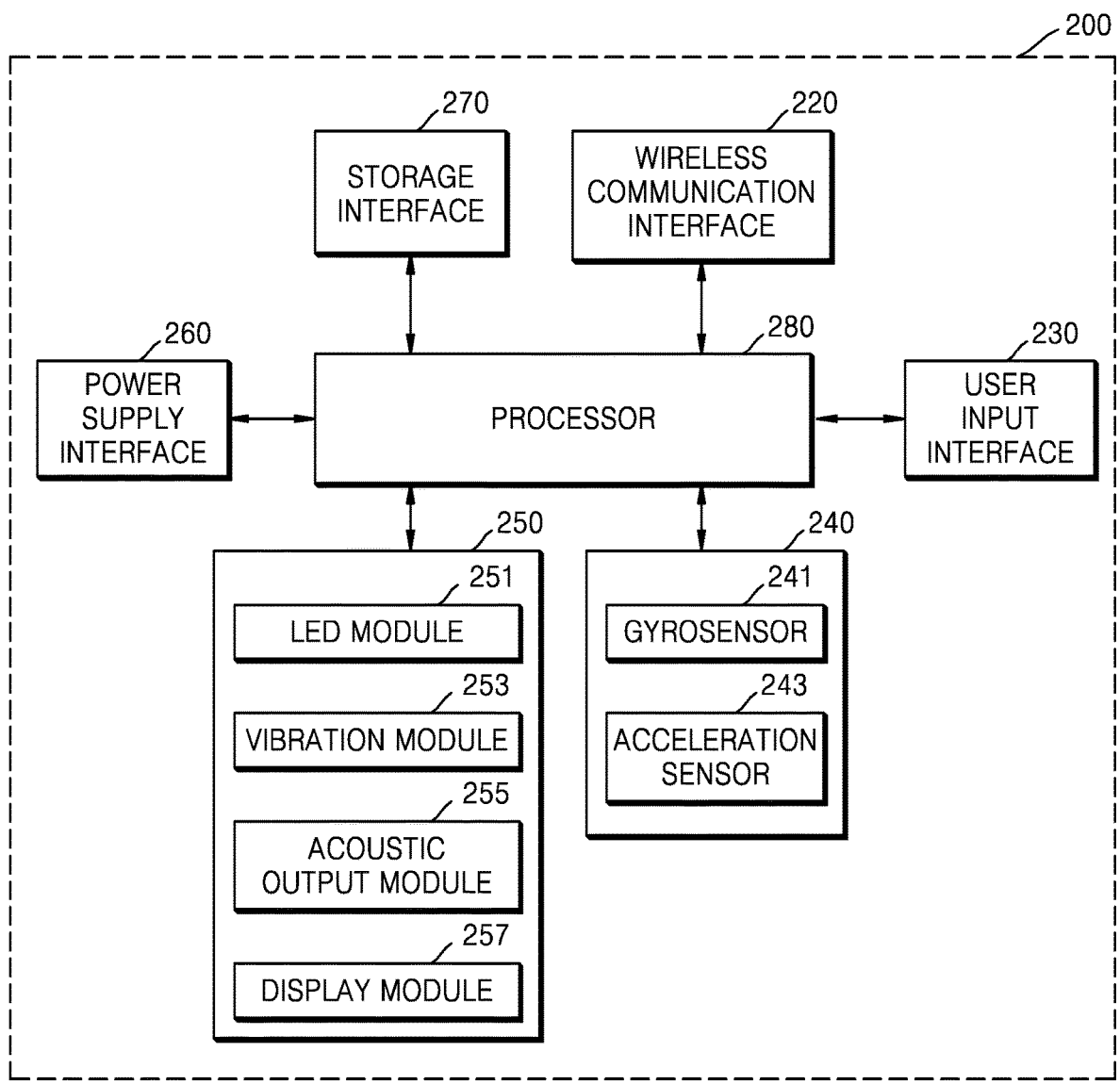
FIG. 28 is a block diagram of a control device according to an example embodiment.

FIG. 28 is a block diagram of a control device related to an example embodiment.

Referring to FIG. 28, the control device 200 may include a wireless communication interface 220, a user input interface 230, a sensor unit 240, an output interface 250, a power supply 260, a storage 270, and a processor 280.

The wireless communication interface 220 may transmit and receive a signal to and from a display device or an external device according to the previous embodiments. The wireless communication interface 220 may include an IR module capable of transmitting and receiving a signal to and from the display device 100 or the external device 300 according to IR communication standard. For example, if necessary, the control device 200 may transmit a command regarding power on/off, channel change, volume change, etc. to the display device 100 or the external device 300 via the IR module.

Alternatively, the wireless communication interface 220 may transmit and receive a signal to and from the display device 100 or the external device 300 by means of WLAN (for example, Wi-Fi), Bluetooth, BLE, ultrasonic waves, Zigbee, etc.

The user input interface 230 may include a keypad, a button, a touch pad, a touchscreen, or the like. A user may manipulate the user input interface 230 to input a command related to the display device 100 or the external device 300 to the control device 200. When the user input interface 230 includes a hard key button, the user may input a command related to the display device 100 or the external device 300 to the control device 200 via a push operation of the hard key button. When the user input interface 230 includes a touchscreen, the user may input a command related to the display device 100 or the external device 300 to the control device 200 by touching a soft key of the touchscreeen.

The sensor unit 240 may include a gyrosensor 241 or an acceleration sensor 243. The gyrosensor 241 may sense information regarding movement of the control device 200. For example, the gyrosensor 241 may sense information regarding an operation of the control device 200 with respect to x, y, and z axes. The acceleration sensor 243 may sense information regarding a movement speed of the control device 200, etc. The sensor unit 240 may further include a distance measuring sensor and thus may sense a distance from the display device 100.

The output interface 250 may output a voice signal or an image corresponding to manipulation of the user input interface 230 or corresponding to a signal received from the display device 100 or the external device 300. The user may recognize manipulation of the user input interface 230 or control of the display device 100 or the external device 300 via the output interface 250.

For example, the output interface 250 may include an LED module that is lit when the user input interface 230 is manipulated or a signal is transmitted and received to and from the display device 100 or the external device 300 via the wireless communication interface 220, a vibration module that generates vibration, an acoustic output module that outputs sound, or a display module that outputs an image.

The power supply 260 supplies power to the control device 200. The power supply 260 may stop power supply when the control device 200 does not move for a predetermined time, thereby reducing power waste. The power supply 260 may resume power supply when a predetermined key included in the control device 200 is manipulated.

The storage 270 may store various types of programs required for control or an operation of the control device 200, application data, etc.

The processor 280 may control may oversee operations of the control device 200 by controlling other components of the control device 200. For example, the processor 280 may transmit a signal corresponding to manipulation of a predetermined key of the user input interface 230 or a signal corresponding to movement of the control device 200 sensed by the sensor unit 240 to the display device 100 or the external device 300 via the wireless communication interface 220.

The processor 280 may transmit a user input signal for inputting at least one of visual condition information of the user and image transformation information to the display device 100. In addition, the processor 280 may transmit a user input signal for changing image transformation information to the display device 100. In addition, the processor 280 may transmit a user input signal for selecting a transformation image to the display device 100.

The example embodiments described herein may be written as a program that may be executed in a computer, and may be implemented in a digital computer that runs the program by using a computer-readable medium. Also, a structure of data used in the example embodiments described herein may be recorded on a computer-readable medium by various methods. Also, the example embodiments described herein may be implemented in the form of a recording medium including a command executable by a computer such as a program module that is executed by a computer. For example, methods implemented as software modules or algorithms may be stored in a non-transitory computer-readable recording medium as program instructions or codes readable and executable by a computer.

The non-transitory computer-readable medium may be any recording medium accessible by a computer, and examples thereof may include volatile and non-volatile media and separable and non-separable media. Examples of the non-transitory computer-readable medium may include a storage medium such as a magnetic storage medium (e.g., ROM, floppy disc, or hard disc), an optically readable medium (e.g., compact disc read-only memory (CD-ROM), or digital versatile disc (DVD)), etc., but are not limited thereto. Also, examples of the non-transitory computer-readable medium may include a computer storage medium and a communication medium.

In addition, computer-readable recording media may be distributed over network-coupled computer systems, and data, for example, program commands and codes, stored in the distributed recording media may be executed by at least one computer.

The particular implementations shown and described herein are illustrative examples and are not intended to limit the scope of the present disclosure in any way. For the sake of brevity, description of conventional electronics, control systems, software development, and other functional aspects of the systems may be omitted.

The above description of the present disclosure is given by way of illustration, and it will be understood by those of ordinary skill in the art that modifications may be readily made therein into other concrete forms without changing the technical spirit or essential features of the present disclosure. Therefore, it should be understood that example embodiments described herein should be considered in a descriptive sense only and not for purposes of limitation. For example, each element described as a single type may be executed in a distributed manner, and elements described as distributed may also be executed in a combined form.

The use of any and all examples, or exemplary language (e.g., "such as") provided herein, is intended merely to describe the present disclosure in detail and does not pose a limitation on the scope of the present disclosure unless otherwise claimed.

In addition, unless elements are specifically described in the present disclosure as "essential," "important," or the like, the elements may not be essential to the practice of the present disclosure.

It will be understood by those of ordinary skill in the art that various changes in form and details may be made in example embodiments of the present disclosure without departing from the spirit and scope as defined by the following claims.

As the present disclosure allows for various changes and numerous example embodiments, the present disclosure is not limit limited to particular modes of practice described herein, and it is to be appreciated that all changes, equivalents, and substitutes that do not depart from the spirit and technical scope of the present disclosure are included in the present disclosure. Therefore, the disclosed example embodiments should be considered in a descriptive sense only and not for purposes of limitation.

The scope of the present disclosure is defined by the appended claims rather than detailed description of the invention, and it is to be appreciated that all changes or changed forms derived from the sense and scope of the appended claims and equivalent concept thereof are included in the present disclosure.

What is claimed is:

1. A display device comprising:
a display;
a camera;
a memory configured to store instructions; and
a processor configured to execute the instructions to:
provide a user interface for obtaining visual condition information comprising information about at least one of a type of visual impairment of a user and a degree of visual impairment according to the type of visual impairment,
obtain an image captured by the camera,
identify an object included in the image,
identify an attribute of the object,
determine first image transformation information comprising a first transformation value regarding enlargement of the object as image transformation information for transforming the image based on the attribute indicating the object is a first object type,
determine second image transformation information comprising a second transform value regarding a location change of the object as the image transformation information for transforming the image based on the attribute indicating the object is a second object type,
transform the image based on the object, the image transformation information and the visual condition information of the user, the visual condition information comprising information about the type of visual impairment of the user, and
display the transformed image on the display.

2. The display device of claim 1, wherein the processor is further configured to execute the instructions to:
obtain the visual condition information via the user interface, and
determine the image transformation information for transforming the image, based on the visual condition information.

3. The display device of claim 2, wherein the memory is further configured to store the image transformation information, the image transformation information being associated with user identification information of the user.

4. The display device of claim 2, wherein the image transformation information comprises a transformation value regarding at least one of the location change of the object, the enlargement of the object, reduction of the object, a color change of the object, a chroma change of the object, and a contrast change of an outline of the object.

5. The display device of claim 1, wherein the object comprises at least one of text, a person, a landscape, and a screen of another display device.

6. The display device of claim 1, wherein the processor is further configured to execute the instructions to:
display, on the display, a first image transformed based on the image transformation information that is set corresponding to the visual condition information,
in response to a first user input, update the image transformation information and display, on the display, a second image transformed based on the updated image transformation information, and
based on a second user input for selecting the second image, associate the updated image transformation information with user identification information of the user.

7. The display device of claim 6, wherein the memory is configured to store the updated image transformation information associated with the user identification information of the user.

8. The display device of claim 1, further comprising a communication interface;
wherein the processor is further configured to execute the instructions to obtain an additional image received from one of an external device via the communication interface and the memory.

9. The display device of claim 1, wherein the processor is further configured to execute the instructions to:
identify an outline of the object, and
transform the image based on the outline.

10. The display device of claim 1, wherein the first object type indicates the object is text, and
wherein the second object type indicates that the object is a person.

11. The display device of claim 1, wherein the first object type indicates the object is text.

12. The display device of claim 1, wherein the second object type indicates the object is a person.

13. The display device of claim 1, wherein the first object type is different than the second object type, and
wherein the first image transformation information is different than the second image transformation information.

14. A method of operating a display device, the method comprising:
providing a user interface for obtaining visual condition information comprising information about at least one of a type of visual impairment of a user and a degree of visual impairment according to the type of visual impairment;

obtaining an image by capturing the image with a camera included in the display device;

identifying an object included in the image;

identifying an attribute of the object;

determining first image transformation information comprising a first transformation value regarding enlargement of the object as image transformation information for transforming the image based on the attribute indicating the object is a first object type;

determining second image transformation information comprising a second transform value regarding a location change of the object as the image transformation information for transforming the image based on the attribute indicating the object is a second object type;

transforming the image based on the object, the image transformation information and the visual condition information of the user, the visual condition information comprising information about the type of visual impairment of the user; and displaying the transformed image on a display of the display device.

15. The method of claim 14, further comprising:

obtaining the visual condition information via the user interface; and determining the image transformation information for transforming the image, based on the obtained visual condition information.

16. The method of claim 15, further comprising storing the image transformation information and associating the determined image transformation information with user identification information of the user.

17. The method of claim 15, wherein the image transformation information comprises a transformation value regarding at least one of the location change of the object, the enlargement of the object, reduction of the object, a color change of the object, a chroma change of the object, and a contrast change of an outline of the object.

18. The method of claim 14, further comprising:

displaying, on the display, a first image transformed based on the image transformation information that is set corresponding to the visual condition information;

in response to a first user input, updating the image transformation information and displaying, on the display, a second image transformed based on the updated image transformation information; and based on a second user input for selecting the second image, associating the updated image transformation information with user identification information of the user.

19. The method of claim 18, further comprising storing the updated image transformation information associated with the user identification information of the user.

20. A non-transitory computer-readable recording medium having recorded thereon instructions which, when executed by a processor, cause the processor to perform operations comprising:

providing a user interface for obtaining visual condition information comprising information about at least one of a type of visual impairment of a user and a degree of visual impairment according to the type of visual impairment;

obtaining an image by capturing the image with a camera included in a display device;

identifying an object included in the image;

identifying an attribute of the object;

determining first image transformation information comprising a first transformation value regarding enlargement of the object as image transformation information for transforming the image based on the attribute indicating the object is a first object type;

determining second image transformation information comprising a second transform value regarding a location change of the object as the image transformation information for transforming the image based on the attribute indicating the object is a second object type;

transforming the image based on the object, the image transformation information and the visual condition information of the user, the visual condition information comprising information about the type of visual impairment of the user; and displaying the transformed image on a display of the display device.

* * * * *